US008889369B2

(12) United States Patent
Dertinger

(10) Patent No.: US 8,889,369 B2
(45) Date of Patent: *Nov. 18, 2014

(54) METHOD FOR THE ENUMERATION OF MAMMALIAN MICRONUCLEATED ERYTHROCYTE POPULATIONS, WHILE DISTINGUISHING PLATELETS AND/OR PLATELET-ASSOCIATED AGGREGATES

(71) Applicant: Litron Laboratories, Ltd., Rochester, NY (US)

(72) Inventor: Stephen D. Dertinger, Webster, NY (US)

(73) Assignee: Litron Laboratories, Ltd., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/075,082

(22) Filed: Nov. 8, 2013

(65) Prior Publication Data

US 2014/0065608 A1 Mar. 6, 2014

Related U.S. Application Data

(60) Continuation of application No. 13/289,764, filed on Nov. 4, 2011, now Pat. No. 8,586,321, which is a (Continued)

(51) Int. Cl.
*G01N 33/00* (2006.01)
*G01N 33/50* (2006.01)
*G01N 33/80* (2006.01)

(52) U.S. Cl.
CPC ......... *G01N 33/5094* (2013.01); *Y10S 435/968* (2013.01); *G01N 33/80* (2013.01);
(Continued)

(58) Field of Classification Search
USPC ............ 435/6, 7.1, 7.2, 7.25, 7.95, 334, 335, 435/287.2, 810, 968, 973; 436/501, 517, 436/521, 522, 536, 10, 63, 172; 530/387.1, 530/388.7
See application file for complete search history.

(56) References Cited

U.S. PATENT DOCUMENTS 4,325,706 A 4/1982 Gershman et al.
4,727,020 A 2/1988 Recktenwald
(Continued)

FOREIGN PATENT DOCUMENTS

EP 0 869 347 10/1998
WO WO 03/016866 2/2003

OTHER PUBLICATIONS

Bowen et al., "Abbot CELL-DYN® 4000 Automated Red Blood Cell Analysis Compared with Routine Red Blood Cell Morphology by Smear Review," Laboratory Hematology 4:45-57 (1998).

(Continued)

*Primary Examiner* — Gail R Gabel
(74) *Attorney, Agent, or Firm* — LeClairRyan, a Professional Corporation

(57) ABSTRACT

A method for the enumeration of micronucleated erythrocyte populations while distinguishing platelet and platelet-associated aggregates involves the use of a first fluorescent labeled antibody having binding specificity for a surface marker for reticulocytes, a second fluorescent labeled antibody having binding specificity for a surface marker for platelets, and a nucleic acid staining dye that stains DNA (micronuclei) in erythrocyte populations. Because the fluorescent emission spectra of the first and second fluorescent labeled antibodies do not substantially overlap with one another or with the emission spectra of the nucleic acid staining dye, upon excitation of the labels and dye it is possible to detect the fluorescent emission and light scatter produced by the erythrocyte populations and platelets, and count the number of cells from one or more erythrocyte populations in said sample. In particular, the use of the second antibody prevents interference by platelet-associated aggregates in the scoring procedures.

18 Claims, 11 Drawing Sheets

Related U.S. Application Data continuation of application No. 12/962,788, filed on Dec. 8, 2010, now Pat. No. 8,076,095, which is a continuation of application No. 12/177,352, filed on Jul. 22, 2008, now Pat. No. 7,867,447, which is a division of application No. 10/878,456, filed on Jun. 28, 2004, now Pat. No. 7,425,421.

(60) Provisional application No. 60/482,678, filed on Jun. 26, 2003.

(52) U.S. Cl.
CPC ................................. *Y10S 435/973* (2013.01)
USPC ............... 435/7.25; 435/6; 435/7.1; 435/7.2; 435/287.2; 435/973; 436/501; 436/517; 436/521; 436/522; 436/10; 436/63; 436/172; 422/73; 422/82.08; 422/82.09; 435/968

(56) References Cited

U.S. PATENT DOCUMENTS

| | | | |
|---|---|---|---|
| 5,858,667 | A | 1/1999 | Dertinger et al. |
| 6,100,038 | A | 8/2000 | Dertinger et al. |
| 6,287,791 | B1 | 9/2001 | Terstappen et al. |
| 7,425,421 | B2 * | 9/2008 | Dertinger ........................ 435/7.25 |
| 8,076,095 | B2 * | 12/2011 | Dertinger ........................ 435/7.25 |
| 8,586,321 | B2 * | 11/2013 | Dertinger ........................ 435/7.25 |
| 2003/0134305 | A1 | 7/2003 | Dertinger et al. |
| 2007/0274919 | A1 | 11/2007 | Dertinger |

OTHER PUBLICATIONS

Supplemental European Search Report from corresponding EP 04777169.6.
Choy et al., "Density-Gradient Enrichment of Newly-Formed Mouse Erythrocytes: Application to the Micronucleus Test, Mutation Research," 130:159-164 (1984).
Riley et al., "Reticulocytes and Reticulocyte Enumeration," J. Clin. Lab. Anal. 15:267-294 (2001).
Weiss, D.J., "Application of Flow Cytometric Techniques to Veterinary Clinical Hematology," Vet. Clin. Pathol. 31(2):72-82 (2002).
Abe et al., "Micronuclei in Human Bone Marrow Cells: Evaluation of the Micronucleus Test Using Human Leukemia Patients Treated with Antileukemic Agents," Mutat. Res. 130:113-120 (1984).
Abramsson-Zetterberg et al., "Human Cytogenetic Biomonitoring Using Flow-Cytometric Analysis of Micronuclei in Transferrin-Positive Immature Peripheral Blood Reticulocytes," Environ. Mol. Mutagen. 36:22-31 (2000).
Abramsson-Zetterberg et al., "The Micronucleus Test in Rat Erythrocytes From Bone Marrow, Spleen and Peripheral Blood: The Response to Low Doses of Ionizing Radiation, Cyclophosphamide and Vincristine Determined by Flow Cytometry," Mutat. Res. 423:113-124 (1999).
Anwar et al., "Chromosomal Aberrations and Micronucleus Frequency in Nurses Occupationally Exposed to Cytotoxic Drugs," Mutagenesis 9:315-317 (1994).
Asanami et al., "The Suitability of Rat Peripheral Blood in Subchronic Studies for the Micronucleus Assay," Mutat. Res. 347:73-78 (1995).
Berg-Drewniok et al., "Increased Spontaneous Formation of Micronuclei in Cultured Fibroblasts of First-degree Relatives of Familial Melanoma Patients," Cancer Genet. Cytogenet. 97:106-110 (1997).
Bhattathiri et al., "Serial Cytological Assay of Micronucleus Induction: A New Tool to Predict Human Cancer Radiosensitivity," Radiother. Oncol. 41:139-142 (1996).
Burrill et al., "Heritability of Chromosome Radiosensitivity in Breast Cancer Patients: A Pilot Study with the Lymphocyte Micronucleus Assay," Int. J. Radiat. Biol. 76(12):1617-1619 (2000).
CAS Registry No. 25535-16-4 (Last Updated Dec. 2000).
CAS Registry No. 67-56-1 (Last Updated May 2006).
CAS Registry No. 9001-99-4 (Last Updated Dec. 2004).
CAS Registry No. 9041-08-1 (Last Updated May 2006).
Choy & Macgregor, "Density-Gradient Enrichment of Newly-Formed Mouse Erythrocytes: Application to the Micronucleus Test," Mutat. Res. 130:159-164 (1984).
Dertinger et al., "Enumeration of Micronucleated CD71-positive Human Reticulocytes with a Single-laser Flow Cytometer," Mutat. Res. 515:3-14 (2002).
Dertinger et al., "Malaria-Infected Erythrocytes Serve as Biological Standards to Ensure Reliable and Consistent Scoring of Micronucleated Erythrocytes by Flow Cytometry," Mutat. Res. 464:195-200 (2000).
Dertinger et al., "Micronucleated CD71-postitive Reticulocytes: A Blood-Based Endpoint of Cytogenetic Damage in Humans," Mutat. Res. 542:77-87 (2003).
Dertinger et al., "Three-Color Labeling Method for Flow Cytometric Measurement of Cytogenetic Damage in Rodent and Human Blood," Environ. Mol. Mutagen. 44:427-435 (2004).
Doneda et al., "High Spontaneous Chromosome Damage in Lymphocytes FromPatients With Hereditary Megaduodenum," Mutat. Res. 348:33-36 (1995).
Fenech, "Biomarkers of Genetic Damage for Cancer Epidemiology," Toxicology 181-182:411-416 (2002).
Fenech, "The Cytokinesis-Block Micronucleus Assay in Nucleated Cells," Mutat. Environ. Part B:195-206 (1990).
Fenech, "The Cytokinesis-Block Micronucleus Technique: A Detailed Description of the Method and its Application to Genotoxicity Studies in Human Populations," Mutat. Res. 285:35-44 (1993).
Goetz et al., "Relationship Between Experimental Results in Mammals and Man. I. Cytogenetic Analysis of Bone Marrow Injury Induced by a Single Dose of Cyclophosphamide," Mutat. Res. 31:247-254 (1975).
Grawé et al., "Evaluation of the Reticulocyte Micronucleus Assay in Patients Treated with Radioiodine for Thyroid Cancer," Mutat. Res. 583:12-25 (2005).
Guo et al., "A Significant Correlation Between Clonogenic Radiosensitivity and the Simultaneous Assessment of Micronucleus and Apoptotic Cell Frequencies," Int. J. Radiation Biol. 75:857-864 (1999).
Hamada et al., "Evaluation of the Rodent Micronucleus Assay by a 28-Day Treatment Protocol: Summary of the $13^{th}$ Collaborative Study by the Collaborative Study Group for the Micronucleus Test (CSGMT)/Environmental Mutagen Society of Japan (JEMS)—Mammalian Mutagenicity Study Group (MMS)," Environ. Mol. Mutagen. 37:93-110 (2001).
Hayashi et al., "An Application of Acridine Orange Fluorescent Staining to the Micronucleus Test," Mutat. Res. 120:241-247 (1983).
Hayashi et al., "In Vivo Rodent Erythrocyte Micronucleus Assay. II. Some Aspects of Protocol Design Including Repeated Treatments, Integration With Toxicity Testing, and Automated Scoring," Environ. Mol. Mutagen. 35:234-252 (2000).
Hayashi et al., "The Micronucleus Assay Using Peripheral Blood Reticulocytes from Mitomycin C- and Cyclophosphamide-Treated Rats," Mutat. Res. 278:209-213 (1992).
Hayashi et al., "The Micronucleus Assay With Mouse Peripheral Blood Reticulocytes Using Acridine Orange-Coated Slides," Mutat. Res. 245:245-249 (1990).
Heddle, "A Rapid in Vivo Test for Chromosome Damage," Mutat. Res. 18:187-190 (1973).
Hillman & Finch, "Erythropoiesis: Normal and Abnormal," Semin. Hematol. 4(4):327-336 (1967).
Hynes et al., "The Single Laser Flow Cytometric Micronucleus Test: A Time Course Study Using Colchicines and Urethane in Rat and Mouse Peripheral Blood and Acetaldehyde in Rat Peripheral Blood," Mutagenesis 17(1):15-23 (2002).
Ilyinskikh et al., "Micronucleus Test of Erythrocytes and Lymphocytes in the Blood of the People Living in the Radiation Pollution Zone as a Result of the Accident at the Siberian Chemical Plant on Apr. 6, 1993," Mutat. Res. 36:173-178 (1996).
Krogh Jensen & Nyfors, "Cytogenetic Effect of Methotrexate on Human Cells In Vivo," Mutat. Res. 64:339-343 (1979).
MacGregor et al. "Clastogen-induced Micronuclei in Peripheral Blood Erythrocytes: The Basis of an Improved Micronucleus Test," Environ. Mutagen. 2:509-514 (1980).

(56) References Cited

OTHER PUBLICATIONS

MacGregor et al., "'Spontaneous' Genetic Damage in Man: Evaluation of Interindividual Variability, Relationship Among Markers of Damage, and Influence of Nutritional Status," Mutat. Res. 377:125-135 (1997).
Maffei et al., "Micronuclei Frequencies in Hospital Workers Occupationally Exposed to Low Levels of Ionizing Radiation: Influence of Smoking Status and Other Factors," Mutagenesis 17:405-409 (2002).
Schlegel & MacGregor, "The Persistence of Micronucleated Erythrocytes in the Peripheral Circulation of Normal and Splenectomized Fischer 344 Rats: Implications for Cytogenetic Screening," Mutat. Res. 127:169-174 (1984).
Schlegel et al., "Assessment of Cytogenetic Damage by Quantitation of Micronuclei in Human Peripheral Blood Erythrocytes," Cancer Res. 46:3717-3721 (1986).
Schmid, "The Micronucleus Test," Mutat. Res. 31:9-15 (1975).
Scott et al., "Radiation-induced Micronucleus Induction in Lymphocytes Identifies a High Frequency of Radiosensitive Cases Among Breast Cancer Patients: A Test for Predisposition?" Br. J. Cancer 77:614-620 (1998).
Smith et al. ("Micronucleated Erythrocytes as an Index of Cytogenetic Damage in Humans: Demographic and Dietary Factors Associated with Micronucleated Erythrocytes in Splenectomized Subjects," Cancer Res. 50:5049-5054 (1990).
Stopper et al., "Pilot Study for Comparision of Reticulocyte-Micronulei with Lymphocyte-Micronuclei in Human Biomonitoring," Toxicol. Letters 156:351-360 (2005).
The Collaborative Study Group for the Micronucleus Test "Micronucleus Test With Mouse Peripheral Blood Erythrocytes by Acridine Orange Supravital Staining: The Summary Report of the 5th Collaborative Study by CSGMT/JEMS•MMS," Mutat. Res. 278:83-98 (1992).
Torous et al., "Comparative Scoring of Mucronucleated Reticulocytes in Rat Peripheral Blood by Flow Cytometry and Microscopy," Tox. Sci. 74:309-314 (2003).
Torous et al., "Enumeration of Micronucleated Reticulocytes in Rat Peripheral Blood: A Flow Cytometric Study," Mutat. Res. 465:91-99 (2000).
Torous et al., "Flow Cytometric Enumeration of Micronucleated Reticulocytes: High Transferability Among 14 Laboratories," Environ. Mol. Mutagen. 38:59-68 (2001).
Torous et al., "Interlaboratory Validation of a CD71-Based Flow Cytometric Method (MicroFlow®) for the Scoring of Micronucleated Reticulosytes in Mouse Peripheral Blood," Environ. Mol. Mutagen. 45:44-55 (2005).
Wakata et al., "Evaluation of the Rat Micronucleus Test with Bone Marrow and Peripheral Blood: Summary of the $9^{th}$ Collaborative study by CSGMT/JEMS MMS," Environ. Mol. Mutagen. 32:84-100 (1998).
Widel et al., "Micronucleus Assay in vivo Provides Significant Prognostic Information in Human Cervical Carcinoma; The Updated Analysis," Int. J. Radiat. Biol. 77(5):631-636 (2001).
Widel et al., "The Increment of Micronucleus Frequency in Cervical Carcinoma During Irradiation In Vivo and Its Prognostic Value for Tumor Radiocurability," Br. J. Cancer 80:1599-1607 (1999).
Zolzer et al., "Changes in S-phase Fraction and Micronucleus Frequency as Prognostic Factors in Radiotherapy of Cervical Carcinoma," Radiother. Oncol. 36:128-132 (1995).

* cited by examiner

METHOD FOR THE ENUMERATION OF MAMMALIAN MICRONUCLEATED ERYTHROCYTE POPULATIONS, WHILE DISTINGUISHING PLATELETS AND/OR PLATELET-ASSOCIATED AGGREGATES

This application is a continuation of U.S. patent application Ser. No. 13/289,764, filed Nov. 4, 2011, now U.S. Pat. No. 8,586,321 issued Nov. 19, 2013, which is a continuation of U.S. patent application Ser. No. 12/962,788, filed Dec. 8, 2010, now U.S. Pat. No. 8,076,095 issued Dec. 13, 2011, which is a continuation of U.S. patent application Ser. No. 12/177,352, filed Jul. 22, 2008, now U.S. Pat. No. 7,867,447 issued Jan. 11, 2011, which is a division of U.S. patent application Ser. No. 10/878,456, filed Jun. 28, 2004, now U.S. Pat. No. 7,425,421 issued Sep. 16, 2008, which claims the benefit of U.S. Provisional Patent Application Ser. No. 60/482,678, filed Jun. 26, 2003, each of which is hereby incorporated by reference in its entirety.

The present invention was made with government support under grant number R44ES010752-02 from the National Institute of Environmental Health Sciences. The government has certain rights in this invention.

FIELD OF THE INVENTION

The present invention relates generally to methods for the enumeration of micronucleated erythrocyte populations, where erythrocyte populations are separately labeled from platelets to discriminate or prevent interference by platelets and/or platelet-associated aggregates in the enumeration thereof.

BACKGROUND OF THE INVENTION

Micronuclei (MN) are formed upon cell division in cells with DNA double-strand break(s) or dysfunctional mitotic spindle apparatus. Based on this detailed understanding of MN origin, the rodent-based micronucleus test has become the most widely utilized in vivo system for evaluating the clastogenic and aneugenic potential of chemicals (Heddle, "A Rapid In Vivo Test for Chromosome Damage," *Mutat. Res.* 18:187-190 (1973); Schmid, "The Micronucleus Test," *Mutat. Res.* 31:9-15 (1975); Hayashi et al., "In Vivo Rodent Erythrocyte Micronucleus Assay: Aspects of Protocol Design Including Repeated Treatments, Integration With Toxicity Testing, and Automated Scoring," *Environ. Mod. Mutagen.* 35:234-252 (2000)). These rodent-based tests are most typically performed as erythrocyte-based assays. Since erythroblast precursors are a rapidly dividing cell population, and their nucleus is expelled a few hours after the last mitosis, MN-associated chromatin is particularly simple to detect in reticulocytes and normochromatic erythrocytes given appropriate staining (e.g., acridine orange) (Hayashi et al., "An Application of Acridine Orange Fluorescent Staining to the Micronucleus Test," *Mutat. Res.* 120:241-247 (1983)).

Target cells for erythrocyte-based micronucleus assays were traditionally obtained from the bone marrow compartment. MacGregor et al. demonstrated that MN formed in the bone marrow of mice persist in peripheral blood ("Clastogen-induced Micronuclei in Peripheral Blood Erythrocytes: The Basis of an Improved Micronucleus Test," *Environ. Mutagen.* 2:509-514 (1980)). Therefore, assay sensitivity is retained when studying genotoxicant-induced micronucleated erythrocytes in the peripheral blood of mice (Hayashi et al., "The Micronucleus Assay With Mouse Peripheral Blood Reticulocytes Using Acridine Orange-Coated Slides," *Mutat. Res.* 245:245-249 (1990); "Micronucleus Test With Mouse Peripheral Blood Erythrocytes By Acridine Orange Supravital Staining: The Summary Report of the 5th Collaborative Study by The Collaborative Study Group for the Micronucleus Test," *Mutat. Res.* 278:83-98 (1992)). To date, peripheral blood MN studies involving species other than the mouse have been qualified because it has been assumed that the high efficiency with which the spleen eliminates MN-containing erythrocytes from circulation would limit assay sensitivity (Schlegel and MacGregor, "The Persistence of Micronucleated Erythrocytes in the Peripheral Circulation of Normal and Splenectomized Fischer 344 Rats: Implications for Cytogenetic Screening," *Mutat. Res.* 127:169-174 (1984)).

Despite a historical bias against the use of peripheral blood, studies with intact rats continue to suggest that circulating reticulocytes represent a suitable target population for studying genotoxicant-induced MN [Hayashi et al., "The Micronucleus Assay Using Peripheral Blood Reticulocytes from Mitomycin C- and Cyclophosphamide-treated Rats," *Mutat. Res.* 278:209-213 (1992); Asanami et al., "The Suitability of Rat Peripheral Blood in Subchronic Studies for the Micronucleus Assay," *Mutat. Res.* 347:73-78 (1995); Wakata et al., "Evaluation of the Rat Micronucleus Test with Bone Marrow and Peripheral Blood: Summary of the 9th Collaborative study by CSGMT/JEMS MMS," *Environ. Mol. Mutagen.* 32:84-100 (1998); Abramsson-Zetterberg et al., "The Micronucleus Test in Rat Erythrocytes From Bone Marrow, Spleen and Peripheral Blood: The Response to Low Doses of Ionizing Radiation, Cyclophosphamide and Vincristine Determined by Flow Cytometry," *Mutat. Res.* 423:113-124 (1999); Torous et al., "Enumeration of Micronucleated Reticulocytes in Rat Peripheral Blood: A Flow Cytometric Study," *Mutat. Res.* 465:91-99 (2000); Hamada et al., "Evaluation of the Rodent Micronucleus Assay by a 28-day Treatment Protocol: Summary of the 13th Collaborative Study by the Collaborative Study Group for the Micronucleus Test (CSGMT)/Environmental Mutagen Society of Japan (JEMS)—Mammalian Mutagenicity Study Group (MMS)," *Environ. Mol. Mutagen.* 37:93-110 (2001); and Hynes et al., "The Single Laser Flow Cytometric Micronucleus Test: A Time Course Study Using Colchicines and Urethane in Rat and Mouse Peripheral Blood and Acetaldehyde in Rat Peripheral Blood," *Mutagenesis* 17:15-23 (2002)). For species with efficient MN-sequestering function such as the rat, it has been suggested that the sensitivity of the endpoint is enhanced when MN analysis is restricted to the most immature fraction of reticulocytes, and also when the number of reticulocytes evaluated is increased (Schlegel and MacGregor, "The Persistence of Micronucleated Erythrocytes in the Peripheral Circulation of Normal and Splenectomized Fischer 344 Rats: Implications for Cytogenetic Screening," *Mutat. Res.* 127:169-174 (1984); Hayashi et al., "The Micronucleus Assay Using Peripheral Blood Reticulocytes from Mitomycin C- and Cyclophosphamide-treated Rats," *Mutat. Res.* 278:209-213 (1992); Abramsson-Zetterberg et al., "The Micronucleus Test in Rat Erythrocytes From Bone Marrow, Spleen and Peripheral Blood: The Response to Low Doses of Ionizing Radiation, Cyclophosphamide and Vincristine Determined by Flow Cytometry," *Mutat. Res.* 423:113-124 (1999); Torous et al., "Enumeration of Micronucleated Reticulocytes in Rat Peripheral Blood: A Flow Cytometric Study," *Mutat. Res.* 465:91-99 (2000); and Abramsson-Zetterberg et al., "Human Cytogenetic Biomonitoring Using Flow-cytometric Analysis of Micronuclei in Transferrin-positive Immature Peripheral Blood Reticulocytes," *Environ. Mol. Mutagen.* 36:22-31 (2000)).

A flow cytometry-based method for simultaneously quantifying the incidence of young and mature erythrocytes, with and without micronuclei, in the peripheral blood compartment of humans has been described previously (Dertinger et al., "Enumeration of Micronucleated CD71-positive Human Reticulocytes with a Single-laser Flow Cytometer," *Mutat. Res.* 515:3-14 (2002)). However, it would be desirable to develop a MN-assay that utilizes a nucleic acid dye with higher specificity for chromatin, is capable of higher rates of analysis, and is capable of preventing platelets and platelet-associated aggregates from interfering with accurate MN measurements.

The present invention is directed to overcoming these and other deficiencies in the art.

SUMMARY OF THE INVENTION

A first aspect of the present invention relates to a method for the enumeration of micronucleated erythrocyte populations while distinguishing platelet and platelet-associated aggregates. This method is carried out by providing a fixed sample comprising erythrocyte populations including mature normochromatic erythrocytes ("NCE"), reticulocytes ("RET"), micronucleated normochromatic erythrocytes ("MN-NCE"), micronucleated reticulocytes ("MN-RET"), or combinations thereof, with the erythrocyte populations being in suspension and substantially free of aggregates, permeable to a nucleic acid dye and RNase, with cell surface markers in a form recognizable by an antibody, and able to exhibit substantially low autofluorescence; substantially degrading RNA of reticulocytes in the fixed sample with RNase; contacting the fixed sample with a first fluorescent labeled antibody having binding specificity for a surface marker for reticulocytes and with a second fluorescent labeled antibody having binding specificity for a surface marker for platelets, wherein the fluorescent emission spectrum of the first and second fluorescent labeled antibodies do not substantially overlap; staining cellular DNA with a nucleic acid staining dye having a fluorescent emission spectrum which does not substantially overlap with the fluorescent emission spectrum of the first and second fluorescent labeled antibodies; exciting the nucleic acid staining dye, the fluorescent label associated with the RET, and the fluorescent label associated with platelets using light of appropriate excitation wavelength for both the nucleic acid staining dye and the fluorescent labels to produce fluorescent emission; and detecting the fluorescent emission and light scatter produced by the erythrocyte populations and platelets, and counting the number of cells from one or more erythrocyte populations in said sample.

According to one approach, each cell in the sample is counted and the total number of each population (e.g., NCE, RET, MN-NCE, MN-RET) is determined.

According to another approach, only RET labeled with the first fluorescent labeled antibody are counted. This is particularly useful when a concentrated cell sample is utilized, there precluding the need to count the vast majority of cells (i.e., NCE) present in the sample. This approach affords a significant faster scoring procedure, given that data acquisition is triggered by the fluorescent label associated with the surface marker for erythroblasts/reticulocytes. Consequently, processing is limited to, e.g., CD71-positive RET, and calculation of the frequency of MN-RET in the sample proceed in otherwise standard fashion.

A second aspect of the present invention relates to a method for the enumeration of micronucleated erythrocyte populations. This method can be carried out by providing a fixed sample comprising erythrocyte populations including NCE, RET, MN-NCE, MN-RET, or combinations thereof, with the erythrocyte populations being in suspension and substantially free of aggregates, permeable to a nucleic acid dye and RNase, with cell surface markers in a form recognizable by an antibody, and able to exhibit substantially low autofluorescence; substantially degrading RNA of reticulocytes in the fixed sample with RNase; contacting the fixed sample with a first fluorescent labeled antibody having binding specificity for a surface marker for reticulocytes; staining cellular DNA with a nucleic acid staining dye having a fluorescent emission spectrum which does not substantially overlap with the fluorescent emission spectrum of the first fluorescent labeled antibody; exciting the nucleic acid staining dye and the fluorescent label associated with the RET using light of appropriate excitation wavelength for both the nucleic acid staining dye and the fluorescent label to produce fluorescent emission; and detecting the fluorescent emission and light scatter produced by the erythrocyte populations, and counting the number of RET and MN-RET in said sample while excluding NCE from said counting.

A third aspect of the present invention relates to a method of assessing the DNA-damaging potential of a chemical agent. This method can be carried out by administering a chemical agent to a mammalian subject and performing the method according to the first or second aspects of the present invention on a peripheral blood or bone marrow sample of the mammalian subject, wherein a significant deviation in the percentage of MN-NCE and/or MN-RET from a baseline MN-NCE and/or MN-RET value in unexposed mammals indicates the genotoxic potential of the chemical agent. Alternately, each subject may contribute a before treatment blood or bone marrow specimen. These specimens thus provide subject-specific MN-RET values against which post-treatment MN-RET values can be compared.

A fourth aspect of the present invention relates to a method of identifying individuals hypersensitive or insensitive to a DNA-damaging agent. This aspect of the present invention can be carried out by administering a DNA-damaging agent to a mammalian subject; and then performing the method according to the first or second aspects of the invention on a peripheral blood or bone marrow sample of the mammalian subject, wherein a significant deviation in the percentage of MN-RET from MN-RET values in similarly exposed mammals considered of "normal sensitivity" would indicate the hypersensitivity or insensitivity of the mammalian subject to the DNA-damaging agent.

A fifth aspect of the present invention relates to a method of measuring safety of individuals exposed to one or more suspected DNA-damaging agents in an environment (workplace or other locales of interest). This aspect of the present invention can be carried out by performing the method according to the first or second aspects of the invention using peripheral blood or bone marrow samples obtained from mammals exposed to one or more DNA-damaging agents in an environment, wherein a significant deviation in the percentage of MN-RET from a baseline MN-RET value in unexposed mammals indicates that the environment contains one or more DNA-damaging agents. Alternately, each subject may contribute a before exposure blood or bone marrow specimen. These specimens thus provide subject-specific MN-RET values against which post-exposure MN-RET values can be compared.

A sixth aspect of the present invention relates to a method of evaluating the effects of an agent which can modify endogenous or exogenous-induced DNA damage. This aspect of the present invention can be carried out by administering an agent that may modify endogenous or exogenous-induced genetic damage to a mammalian subject; and then performing the method according to the first or second aspects of the invention on a peripheral blood or bone marrow sample of the mammalian subject, wherein a significant deviation in the percentage of MN-RET from MN-RET values in mammals which are similarly treated except for the suspected modulating agent indicates that the agent can modify endogenous or exogenous-induced DNA damage. Alternately, each subject may contribute a before treatment blood or bone marrow specimen. These specimens thus provide subject-specific MN-RET values against which post-treatment MN-RET values can be compared.

A seventh aspect of the present invention relates to a method of evaluating the effects of a diet or a dietary nutrient which can modify endogenous or exogenous-induced DNA damage. This aspect of the present invention can be carried out by subjecting a mammal to a predetermined diet or a dietary nutrient that may modify endogenous or exogenous-induced DNA damage; and then performing the method according to the first or second aspects of the invention on a peripheral blood or bone marrow sample of the mammal, wherein (i) a significant deviation in the percentage of MN-RET from baseline MN-RET values in unexposed mammals indicates that the diet or dietary nutrient can modify endogenous DNA damage; or (ii) a significant deviation in the percentage of MN-RET from MN-RET values in mammals treated with the same genotoxicant but without the predetermined diet or the dietary nutrient indicates that the diet or the dietary nutrient can modify exogenous DNA damage.

An eighth aspect of the present invention relates to a method of evaluating the effects of a mutation or gene polymorphism which can modify endogenous or exogenous-induced DNA damage. This aspect of the present invention can be carried out by obtaining DNA sequence information for one or more genes of interest for a mammalian subject; and then performing the method according to the first or second aspect of the invention on a peripheral blood or bone marrow sample of the mammalian subject, wherein a significant deviation in the percentage of MN-RET values in mammals with a mutation or gene polymorphism compared to MN-RET values in similarly treated mammals with a wildtype genotype indicates that the mutation or gene polymorphism can modify endogenous or exogenous-induced DNA damage.

A ninth aspect of the present invention relates to a method of measuring the level of DNA damage following exposure of individual(s) to a DNA damaging agent. This aspect of the present invention can be carried out by performing the method according to the first or second aspects of the invention on a peripheral blood or bone marrow sample of a mammal exposed to a DNA damaging agent, wherein a significant deviation in the percentage of MN-RET from a baseline MN-RET value in unexposed mammals indicates that the agent caused DNA damage and wherein greater deviation from the normal percentage indicates the level of the DNA damage. Alternately, each subject may contribute a before treatment blood or bone marrow specimen. These specimens thus provide subject-specific MN-RET values against which post-treatment MN-RET values can be compared.

A tenth aspect of the present invention relates to a method of assessing asplenia or hyposplenic function. This aspect of the present invention can be carried out by performing the method according to the first or second aspects of the invention on a peripheral blood sample of a mammal, wherein either (i) a significant deviation in the percentage of MN-NCE from a baseline MN-NCE value in normal mammals possessing a healthy functional spleen, (ii) a ratio of MN-RET frequency to MN-NCE frequency is less than about 20, or (iii) both (i) and (ii), indicates asplenia or hyposplenic function. This aspect of the present invention can be used to assess splenic dysfunction that is associated with a disease state, or which results from exposure to toxic agent(s).

An eleventh aspect of the present invention relates to a method of assessing the efficacy of drugs or other interventions such as dietary changes for preventing or delaying the onset of asplenia or hyposplenic function. This aspect of the present invention can be carried out by performing the method according to the first or second aspects of the invention on a peripheral blood sample of a mammal, wherein the change in MN-NCE frequency over time and/or the ratio of MN-RET frequency to MN-NCE frequency is compared to a historical database which describes the typical rate at which these values increase for subjects with the same disease or condition associated with asplenia or hyposplenic function. Efficacy would then be indicated by a lower rate of change to MN-NCE frequency, and/or the MN-RET to MN-NCE ratio. Alternately, efficacy could be determined by grouping subjects with similar diseases or conditions known to result in asplenia or hyposplenic function into treatment and placebo groups. Efficacy would be exhibited by a lower rate of MN-NCE increase, and/or a lower rate of increase to the ratio MN-RET to MN-NCE for those subjects undergoing treatment with the presumptive protecting agent.

A twelfth aspect of the present invention relates to a method whereby erythrophagocytic activity measurements provide prognostic information regarding the likely severity of diseases or conditions associated with hyposplenism or functional asplenia. This aspect of the present invention can be carried out by performing the method according to the first or second aspects of the invention on a peripheral blood sample of a mammal, wherein the change in MN-NCE frequency over time and/or the ratio of MN-RET frequency to MN-NCE frequency is compared to a historical database which describes the typical rate of change for subjects with the same disease or condition associated with asplenia or hyposplenic function. Significant departures from this average rate of change likely reflects accumulated damage to the spleen, which in turn may be representative of global organ damage. Subjects that have elevated MN-NCE and/or MN-RET to MN-NCE ratios early in life, or which change substantially over a short period of time may be predicted to have a more severe form of the disease, whereby more vigorous interventions may be indicated. Conversely, subjects whose MN-NCE and/or MN-RET to MN-NCE ratios rise appreciably more slowly than usual for these diseases and conditions may be less at risk for complications and therefore less aggressive monitoring and/or intervention may be desirable.

A thirteenth aspect of the present invention relates to a method of assessing anemia. This aspect of the present invention can be carried out by performing the method according to the first or second aspects of the invention on a peripheral blood or bone marrow sample of a mammal, wherein a significant deviation in the percentage of MN-RET from a baseline MN-RET value in normal mammals assists the differential diagnosis of anemia.

A fourteenth aspect of the present invention relates to a method of assessing severity of a disease or disorder associated with hyposplenic function. This aspect of the present invention can be carried out by performing the method according to the first or second aspect of the invention on a peripheral blood sample of a human having a disease or disorder associated with hyposplenic function; and then determining a ratio of micronucleated reticulocyte frequency to micronucleated normochromatic erythrocyte frequency, wherein severity of the disease or disorder is indicated by the smaller the ratio is when less than about 20.

A fifteenth aspect of the present invention relates to a kit that includes one or more reagents for practicing the various aspects of the present invention. The kit preferably includes, a first container holding a solution that includes a first antibody that recognizes a cell surface marker for reticulocytes; a second container holding a solution that includes a second antibody that recognizes a cell surface marker for platelets; and a third container holding a nucleic acid dye.

The labeling/staining procedure described in the current report prevents platelets and platelet-associated aggregates from affecting MN measurements, and is based on a nucleic acid dye with higher specificity for DNA. Significantly, the scoring system described herein quantifies MN frequency in the most immature fraction of RET, and accomplishes this at previously unattainable rates of speed. Beyond describing an improved methodological approach for enumerating MN-RET, this report includes data from experiments which indicates that exposure to known DNA-damaging agents induce MN-RET which can be detected in peripheral blood circulation of eusplenic humans. Beyond describing an improved methodological approach for enumerating MN-NCE, this report includes data from experiments which indicates that spleen dysfunction stemming from vaso-occlusive events results in elevated MN-NCE frequencies which can be detected in peripheral blood circulation of humans.

BRIEF DESCRIPTION OF THE DRAWINGS

FIG. 9B corresponds to sickle cell anemia patients with the generally mild form of the disease, HbSC. The significant age-dependent increase in MN-NCE values observed for young HbSS patients is likely related to the degree to which accumulated vaso-occlusive damage has destroyed splenic architecture and filtration function. Regarding HbSC disease, only two of twelve patients exhibited MN-NCE values that are suggestive of splenic dysfunction.

DETAILED DESCRIPTION OF THE INVENTION

Figure 1:
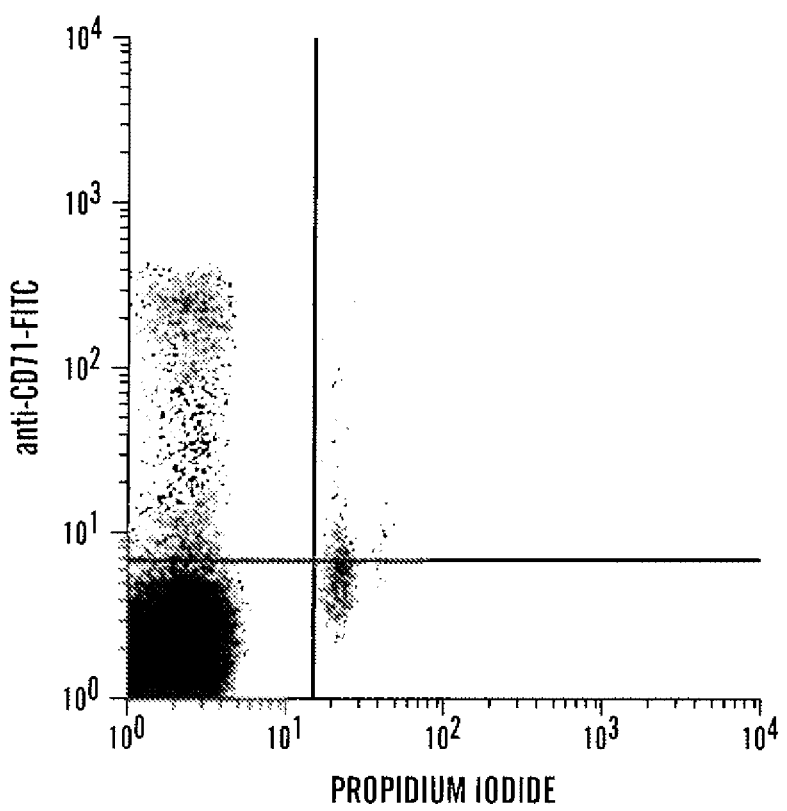
FIG. 1 is a bivariate graph of malaria-infected rat blood. Green fluorescence associated with CD71 expression is graphed on the y-axis, and red fluorescence associated with DNA content is graphed on the x-axis. Note that nucleated cells, which fall in the fourth decade of propidium iodide fluorescence, have been excluded from this plot based on their high (2n) DNA content. Malaria-infected blood was stained in parallel with test samples and analyzed at the beginning of each day of analysis. These samples were used to set appropriate PMT voltages and electronic compensation. As malaria-infected erythrocytes mimic the DNA content of micronucleated erythrocytes, they also served to guide the position of the quadrant that was used to distinguish erythrocytes with and without micronuclei.

The present invention is directed to a method for the enumeration of micronucleated erythrocyte populations using an optical device designed for illumination and analysis of blood samples.

For purposes of the present invention, "erythrocyte populations" is intended to include, among other blood cells, populations of NCE, RET, MN-NCE, MN-RET, and combinations thereof. Samples of erythrocyte populations from mammals can be obtained from either peripheral blood or bone marrow. The erythrocyte populations from any mammal can be analyzed in accordance with the present invention, although preferred mammals include, without limitation, rodents, such as rat and mouse; canines, such as beagle dogs; and primates such as monkeys, chimpanzees, and humans. As for the source of mammalian erythrocytes, conventional procedures can be utilized to obtain samples. For example, a blood sample can be obtained from the tail vein of rodents after a brief warming period under a heat lamp. Alternately, cardiac puncture may be performed on anesthetized animals. In the case of humans, a finger prick with a lancet or a blood draw via standard venipuncture are convenient sources of erythrocytes. In any case, blood should be collected into an anticoagulant (e.g., EDTA or heparin) to prevent aggregation and clot formation. Bone marrow samples can also be acquired according to standard procedures. Standard buffers which do not lead to cellular aggregation or clotting should be utilized with bone marrow samples. The samples can also be treated in a manner that affords enrichment of the erythrocyte populations to be examined (Abramsson-Zetterberg et al., "Human Cytogenetic Biomonitoring Using Flow-Cytometric Analysis of Micronuclei in Transferrin-Positive Immature Peripheral Blood Reticulocytes," *Environ. Mol. Mutagen.* 36:22-31 (2000); Choy and MacGregor, "Density-gradient Enrichment of Newly-Formed Mouse Erythrocytes: Application to the Micronucleus Test," *Mutat. Res.* 130:159-164 (1984), which is hereby incorporated by reference in its entirety), although enrichment is a less preferred approach given that additional steps are required and the enrichment process may skew the results of any frequency analysis.

Even when sample collection occurs in a manner designed to reduce the likelihood of gross clot formation, some degree of platelet-platelet and platelet-cell aggregation often occurs (hereafter referred to as "platelet-associated aggregates"). These events have the potential to interfere with the accurate enumeration of red blood cell populations, including MN-containing erythrocytes. It would be desirable, therefore, to provide a means for discriminating platelet-associated aggregates, and even singular platelets, from red blood cells of interest (i.e., NCE, RET, MN-NCE, and MN-RET). A method which labels platelets, but not red blood cells, with a fluorochrome-conjugated antibody is an advantageous means for accomplishing this, as it eliminates the need for processing steps designed to physically separate red blood cells from platelets.

Once a blood or bone marrow sample has been obtained, the sample is fixed so as to render the blood cells in suspension and preferably substantially (but not necessarily completely) free of aggregates, permeable to a nucleic acid dye and RNase, with cell surface markers intact (i.e., in a form recognizable by appropriate antibodies), and exhibiting substantially low autofluorescence. Fixing is accomplished in alcohol at a temperature of about −40° C. to about −90° C. Briefly, a 100 to 1000 µl aliquot of each blood suspension (e.g., from a syringe and needle or from a pipettor) is delivered forcefully into tubes containing a suitable amount (e.g., about 1 to about 11 ml) of ultracold alcohol. It is preferable that the ultracold alcohol fixative is maintained at about −40° C. to about −90° C., preferably about −70° C. to about −90° C. The alcohol may be a primary alcohol or a secondary alcohol. Suitable primary alcohols include but are not limited to ethanol and methanol. Suitable secondary alcohols include but are not limited to isopropyl alcohol. Of these alcohols, methanol is preferred. Once the samples are fixed, the tubes can be struck sharply or vortexed to break up aggregates. The samples can be stored at about −40° C. to about −90° C., preferably about −70° C. to about −90° C. The samples are preferably stored overnight (e.g., between about 8-15 hours) prior to analysis.

Prior to analysis, the cells are diluted out of the fixative with ice cold buffered salt solution. In a preferred embodiment, the buffered salt solution is Hank's Balanced Salt Solution (HBSS), or about 0.9% NaCl supplemented with sodium bicarbonate, preferably at about 5.3 mM. The cells are centrifuged under conditions which are effective at maintaining cell structure while removing dissolved solids therefrom. Exemplary centrifugation conditions include about 500× to about 1000×g for about 5 minutes. Thereafter, supernatants are decanted and the cell pellets can be stored at about 4° C. or on ice until analysis. Once cells are washed out of alcohol fixative, it is preferable to stain and analyze them within about 3 days, more preferably on the same day that they are washed out of fixative.

Once the cells are washed out of fixative, RNA of the reticulocytes is substantially degraded with RNase so that the only nucleic acid that remains is DNA (i.e., DNA of micronuclei or Howell-Jolly bodies, if present). RNase treatment can be carried out by introducing fixed and washed erythrocyte populations into tubes containing an appropriate amount of an RNase A solution (i.e., ~20 µg RNase/ml HBSS). Incubations with RNase are preferably carried out at about 4° C. to about 25° C.

Following RNase treatment, nucleic acid dyes are used to stain DNA of micronuclei present in erythrocytes or reticulocytes and fluorescent labeled antibodies directed to specific cell surface markers are used to distinguish reticulocytes from more mature erythrocytes, platelets, and platelet-associated aggregates, as well as to distinguish one sub-population from another sub-population within the larger erythrocyte population. Alternatively, RNase treatment and antibody marking of reticulocytes and platelets can be carried out simultaneously.

One type of antibody employed in the present invention has binding specificity for a surface marker for reticulocytes and includes a fluorescent label with a fluorescent emission pattern that is detectable by the optical detection equipment employed. As used herein, "a surface marker for erythroblasts/reticulocytes" means at least one species of a surface antigen present on reticulocytes but absent on mature erythrocytes, thereby enabling reticulocytes (and erythroblasts) to be distinguished from mature erythrocytes by the presence of this marker. Such markers are known in the art to include, but are not limited to, CD71 (a transferrin receptor). It should be appreciated by those of ordinary skill in the art that other reticulocyte cell surface markers have been and may continue to be identified, and antibodies directed to such markers can likewise be employed.

Another type of antibody employed in the present invention has binding specificity for a surface marker for platelets and includes a fluorescent label with a fluorescent emission pattern that is detectable by the optical detection equipment employed. As used herein, "a surface marker for platelets" means at least one species of a surface antigen present on platelets but absent on reticulocytes and erythrocytes, thereby enabling platelets to be distinguished by the presence of this marker. Such markers are known in the art to include, but are not limited to, CD9, CDw17, CD29, CD31, CD32, CD41, CD42a, CD42b, CD42c, CD42d, CD43, CD46, CD49f, CD51, CD60a, CD61, CD62P, CD63, CD69, CD82, CD98, CD102, CD110, CD112, CDw119, CD120a, CD128a, CD128b, CD130, CD132, CD140a, CD141, CD148, CD151, CD165, CD184, CD226, and CD245. It should be appreciated by those of ordinary skill in the art that other platelet surface markers have been and may continue to be identified, and antibodies directed to such markers can likewise be employed.

In addition to the use of whole antibodies (e.g., polyclonal or monoclonal antibodies), it should be appreciated that whole antibodies can be substituted by using binding portions of such antibodies. Such binding portions include, without limitation, Fab fragments, F(ab')$_2$ fragments, and Fv fragments. As used herein, Fab fragments, F(ab')$_2$ fragments, and Fv fragments are functional equivalents of whole antibodies.

A number of fluorescent labels are available which have the desired excitation and emission characteristics. As used herein, the term "fluorescent label" means at least one species of a fluorescent molecule that is conjugated or otherwise attached to a monoclonal antibody with binding specificity for a surface marker for erythroblasts/reticulocytes or a surface marker for platelets. Because optical detection equipment is intended to be employed with the present invention, the selected fluorescent label used on the antibodies should accommodate the excitation parameters of the illuminating light source employed in the optical detection equipment.

Where multiple antibodies are used to label different erythrocyte sub-populations and even other events such as platelets and platelet-associated aggregates, then it is desirable to utilize different fluorescent labels on each type of antibody, such that each label has an emission spectrum which does not substantially overlap the emission spectra of other labels. Preferably, each has a sufficiently distinct emission maxima that discriminates itself from other fluorescent labels.

Generally, fluorescent labels having an excitation wavelength that is matched to the wavelength of illuminating light, which is typically in the range of about 485 to about 491 nm. The fluorescent labels can have any that can be detected by an appropriate detector device. By way of example, many fluorescent labels have an emission maxima in a range of about 510 to about 750 nm. Suitable fluorescent labels include, but are not limited to fluorescein isothiocyanate (FITC), Alexa Fluor 488, phycoerytherin (PE), PE-Texas Red, PE-Cy5, PerCP, PerCP-Cy5.5, and PE-Cy7.

A preferred fluorescent labeled antibody directed to a surface marker for erythroblasts/reticulocytes (i.e., discriminating between RET and mature erythrocytes) is anti-CD71-FITC antibody.

A preferred fluorescent labeled antibody directed to human platelets or platelet-associated aggregates is anti-CD42b-PE. A preferred fluorescent labeled antibody directed to rodent platelets or platelet-associated aggregates is anti-CD61-PE.

Labeling of erythroblast/reticulocyte and/or platelets and platelet-associated aggregates with selected fluorescent labeled antibodies is achieved by combining antibody solution with the fixed and washed mammalian blood (or bone marrow) sample under conditions effective to allow antibodies to recognize the cell or platelet surface markers. Exemplary conditions include an approximately 30 minute incubation period at about 4° C. Thereafter, sample can be washed using, e.g., buffered saline solution or HBSS (with or without fetal bovine serum, at about 1% volume/volume).

Suitable nucleic acid dyes are those capable of staining cellular DNA at a concentration range detectable by the optical detection equipment and which have a fluorescent emission spectrum which does not substantially (i.e., significantly) overlap with the fluorescent emission spectrum of the fluorescent labels used on antibodies. A preferred nucleic acid dye is propidium iodide. It should be appreciated by those of ordinary skill in the art that other nucleic acid dyes are known in the art and are continually being identified. Any suitable nucleic acid dye with appropriate excitation and emission patterns can be utilized herein.

Washed antibody-labeled cells can be resuspended with a nucleic acid dye solution (e.g., dilution of dye stock solution in HBSS). Nucleic acid dyes are available from a number of suppliers in crystalline form or as highly concentrated stock solutions. It is desirable to work with nucleic acid dyes once cell density and dye concentration parameters have been optimized through routine experimentation as described in the Examples infra.

Thereafter, the treated sample can be subjected to optical detection of the micronucleated erythrocyte populations.

The optical detection systems have one or more light sources, preferably in the form of one or more amplified or collimated beams of light, that are able to excite the nucleic acid dye(s) and fluorescent labeled antibodies; and one or more detectors that are able to detect the fluorescence emissions caused by the nucleic acid dye(s) and the fluorescent labeled antibodies. Suitable optical detection systems include, without limitation, single-laser flow cytometers; dual- or multiple-laser flow cytometers; and hematology analyzers equipped with an appropriate illumination device (e.g., diode, laser, etc.).

Single-laser flow cytometric analysis uses a single focused laser beam with an appropriate emission band to excite the nucleic acid dye(s) and the fluorescent labeled antibodies. As cells pass through the focused laser beam, the cells bound by anti-reticulocyte/erythroblast antibody exhibit a fluorescent emission maxima characteristic of the fluorescent label associated therewith, cells possessing a micronucleus exhibit a fluorescent emission maxima characteristic of the nucleic acid dye, and events (i.e., platelets or platelet-associated aggregates) bound by anti-platelet antibody exhibit a fluorescent emission maxima characteristic of the fluorescent label associated therewith. The flow cytometer is equipped with appropriate detection devices to enable detection of the fluorescent emissions and light scatter produced by the erythrocyte populations and the platelets. Cells are counted and the number of specific erythrocyte sub-populations in the sample can be counted and, importantly, discriminated from platelets and platelet-associated aggregates.

Dual- or multiple-laser flow cytometric analysis use two or more focused laser beams with appropriate emission bands, in much the same manner as described above for the single-laser flow cytometer. Different emission bands afforded by the two or more lasers allow for additional combinations of nucleic acid dye(s) and fluorescent labeled antibodies.

Prior to such excitation and detection of fluorescence from the treated samples, the optical detection system can be calibrated for the detection of micronuclei. This can be achieved using a biological standard which has been treated in parallel with the fixed sample (i.e., RNase, antibody treatment, nucleic acid stain, etc.). Preferred biological standards are fixed erythrocyte samples obtained from a malaria-infected mammal, more preferably a *Plasmodium berghei*-infected rodent (e.g., rat or mouse). The use of the biological standard mimics the micronucleated erythrocytes. As a result of the use of such biological standards to calibrate a flow cytometer, for example, it is possible to achieve one or more of the following: setting photomultiplier tube voltage, setting electronic compensation parameters, and defining the position of regions that indicate micronucleus-containing erythrocytes.

According to a modified approach for using high density cell samples, it is possible to utilize the presence of the surface marker for erythroblasts/reticulocytes as a means for excluding cells (e.g., mature erythrocytes) to be counted. Because mature erythrocytes make up the predominant cell sub-population, it is possible to exclude those cells from counting and thereby improve the speed of collecting data on a particular sample. For example, it becomes possible to screen samples having densities greater than about 30 million cells/ml, more preferably greater than about 50 million cells/ml, most preferably greater than 80 million cells/ml. As a consequence, the time for counting cells in a sample can be significantly reduced. This approach can be carried out either with or without the use of an antibody that recognizes a surface marker for platelets.

The present inventions will find myriad uses in the field of toxicity, and in particular, the field of genetic toxicology. For example, the present inventions will be useful for studying (i) whether chemical or physical agents damage DNA, (ii) whether chemical or physical agents protect against endogenous or exogenous DNA damage, (iii) whether chemical or physical agents potentiate endogenous or exogenous DNA damage, (iv) whether mutations and/or genetic polymorphisms lead to increased endogenous or exogenous DNA damage, and (v) whether mutations and/or genetic polymorphisms lead to decreased endogenous or exogenous DNA damage. In using the methods of the present inventions to assess endogenous or exogenous DNA damage, or for evaluating the influence of modulating agents or genotypes on endogenous or exogenous DNA damage, determinations of such effects are typically based on statistically significant differences as measured using appropriate statistical analyses.

General experimental design considerations for evaluating DNA damaging agents according to the present inventions would involve administering the agent to a mammal prior to obtaining one or more blood samples. The administering of the DNA-damaging agent can be performed anywhere from about 1 to about 4 days, preferably about 2 to 4 days, prior to obtaining the blood sample. Additionally, one or more pre-exposure blood sample may be obtained, and would serve as a subject-specific control for evaluating treatment related changes to MN-RET frequency. To monitor the modulating effects of a suspected modulating agent, the suspected modulating agent can be administered to the individual simultaneous or contemporaneous with administration of the DNA-damaging agent. By contemporaneous, administration of the modulating agent is intended to occur before, after, or both before and after administration or exposure to the DNA damaging agent. Preferably, contemporaneous administration occurs within about 12 hours (i.e., before and/or after). Any modulating effect afforded by the agent can be measured relative to damage caused in the absence of the suspected modulating agent or to historical data based on the degree of damage normally afforded by the DNA-damaging agent.

Therefore, the present inventions can be used to assess the DNA-damaging potential of a chemical agent (e.g., a pharmaceutical agent) by administering the chemical agent to a mammalian subject and then performing the analysis of the present inventions on a sample from a mammalian subject, wherein a significant deviation in the percentage of MN-RET from a baseline MN-RET value in an unexposed subject (i.e., placebo-receiving mammalian subject) indicates the genotoxic potential of the chemical agent. The greater the deviation from the baseline value, the greater the extent or level of damage caused by the chemical agent. Alternately, each subject may contribute one or more before-treatment blood or bone marrow specimen. These specimens thus provide subject-specific MN-RET values against which post-treatment MN-RET values can be compared. Examples of chemicals that damage DNA include, but are not limited to: inorganic genotoxicants (e.g., arsenic, cadmium and nickel), organic genotoxicants (especially those used as antineoplastic drugs, e.g., cyclophosphamide, cisplatin, vinblastine, cytosine arabinoside, etc.), anti-metabolites (especially those used as antineoplastic drugs, e.g., methotrexate and 5-fluorouracil), organic genotoxicants that are generated by combustion processes (e.g., polycyclic aromatic hydrocarbons such as benzo(a)pyrene), as well as organic genotoxicants that are found in nature (e.g., aflatoxins such as aflatoxin B1).

Likewise, the present inventions can be used to assess the DNA-damaging potential of a physical agent (e.g., ionizing radiation) by administering the physical agent to a mammalian subject and then performing the analysis of the present inventions on a sample from a mammalian subject, wherein a significant deviation in the percentage of MN-RET from a baseline MN-RET value in an unexposed subject (i.e., sham-exposed mammalian subject) indicates the genotoxic potential of the physical agent. The greater the deviation from the baseline value, the greater the extent or level of damage caused by the physical agent. Alternately, each subject may contribute one or more before-treatment blood or bone marrow specimen. These specimens thus provide subject-specific MN-RET values against which post-treatment MN-RET values can be compared. Examples of physical agents known to cause DNA damage include, but are not limited to: gamma radiation, beta radiation, and UV radiation.

Such monitoring can be used to identify individuals who are hypersensitive or refractory to endogenous or exogenous DNA-damage. Analyses performed according to the present inventions would be conducted on a sample from a mammalian subject, wherein a significant deviation in the percentage of MN-RET from MN-RET values in similarly treated mammals considered of "normal sensitivity" would indicate the degree of hypersensitivity or insensitivity. When DNA sequence data are available and combined with MN-RET measurements provided by the present inventions, then it becomes possible to identify mutations and/or genetic polymorphisms that convey hypersensitivity or insensitivity phenotypes for endogenous or exogenous DNA-damage.

Furthermore, as part of a routine protocol following an adverse event in a particular environment (e.g., radiation leak or carcinogenic agent spill), such monitoring can be used to define the extent of harm an environment presents as well as the successfulness of any cleanup. The affected environment is typically, but not necessarily limited to, a workplace environment. These monitoring approaches can be carried out by performing the analysis of the present inventions using samples obtained from mammals exposed to one or more DNA-damaging agents in the affected environment, wherein a significant deviation in the percentage of MN-RET from a baseline MN-RET value in unexposed mammals indicates that the affected environment contains one or more DNA-damaging agents. In addition, the level of damage caused by such agents to which the mammals were exposed indicates the severity of contamination to the affected environment. Alternately, each subject may contribute one or more before-exposure blood or bone marrow specimen. These specimens thus provide subject-specific MN-RET values against which post-exposure MN-RET values can be compared.

Because of the interaction of agents, it is possible that certain agents may offer protective benefit while other agents may present a magnified risk when combined. For this reason, the present inventions can be used to evaluate the effects of an agent which can modify (i.e., enhance or suppress) endogenous or exogenous-induced DNA damage. This can be achieved by subjecting mammals to a suspected modulating agent with or without exposure to an exogenous agent that can induce DNA damage and then performing the analysis of the present inventions on a sample from the subject. A significant deviation in the percentage of MN-RET from baseline MN-RET values in unexposed mammals indicates that the agent can modify endogenous DNA damage; a significant deviation in the percentage of MN-RET from MN-RET values in mammals treated with the same exogenous genotoxicant but without the modifying agent indicates that the agent can modify exogenous DNA damage. A reduction in the percentage of MN-RET compared to baseline figures indicates a suppression of DNA-induced damage, whereas an increase in the percentage of MN-RET indicates an enhancement of DNA-induced damage.

Putative protective agents can be vitamins, bioflavonoids and anti-oxidants, dietary supplements (e.g., herbal supplements), and dietary adjustments (e.g., diets high in beneficial foods and low in processed foods), or any other protective agent, naturally occurring or synthesized by man.

As noted above, diet and dietary nutrients are one type of potentially protective agents. Thus, another aspect of the invention relates to a method of evaluating the effects of a diet or a dietary nutrient which can modify endogenous or exogenous-induced DNA damage. This can be achieved by subjecting a mammal to a predetermined diet or a dietary nutrient that may modify endogenous or exogenous-induced DNA damage, either with or without exposure to exogenous agents that can induced DNA damage. The analysis of the present inventions is performed on samples from the mammal, wherein a significant deviation in the percentage of MN-RET from a baseline MN-RET value in unexposed mammals indicates that the diet can modify endogenous DNA damage. A significant deviation in the percentage of MN-RET from MN-RET values in mammals treated with the same exogenous genotoxicant but without the diet or dietary nutrient indicates that the diet or dietary nutrient can modify exogenous DNA damage.

Further aspects of the present inventions relate to its use for diagnosis and the monitoring of certain diseases. Whereas in the field of toxicology and genetic toxicology red blood cell inclusions formed of chromatin are known as micronuclei, the field of medical hematology has known them as Howell-Jolly bodies ("HJB"). In the medical hematology field, when HJB are observed upon microscopic inspection of peripheral blood smears, they are considered evidence of dysfunctional (or missing) spleen, or of certain disease states. For instance, HJB are observed at high frequencies in patients with Megaloblastic anemia. Thus, differentiating this type of anemia from others can in part be aided by an assessment of HJB frequency. For instance, if Pernicious anemia (a type of Megaloblastic anemia) is suspected, then B12 administration is indicated. One way of assessing whether the diagnosis was correct and whether treatment has been effective would be to use the present inventions to evaluate the frequency of MN-RET and/or MN-NCE before and over the course of therapy.

Another use of the present inventions in the area of clinical diagnosis or patient monitoring is assessment of spleen function. The human spleen is primarily responsible for eliminating HJB-containing red blood cells. In fact, the healthy human spleen is able to reduce HJB-containing erythrocytes from an average of about 0.1% to about 0.3% in the bone marrow, and to about 0.002% in peripheral blood circulation. Thus, when the frequency of HJB-containing normochromatic erythrocytes (MN-NCE) increases, this is indicative of splenic dysfunction. There are disease-related states that can result in compromised splenic function. These conditions are important to detect, since subjects with asplenia or hyposplenic function can be at increased risk of infection by encapsulated organisms such as pneumococci, *Haemophilus influenzae*, and meningococci. These patients are also more susceptible to infections with intra-erythrocytic organisms such as *Babesia microti* and those that seldom affect healthy people, such as *Capnocytophaga canimorsus*. This is why, for instance, patients with sickle cell disease are often prophylactically treated with antibiotics to compensate for the spleen dysfunction which occurs as a secondary result of their disease. Other disease states that are associated with functional asplenia or hyposplenic function include: Celiac disease, cirrhosis with or without portal hypertension, vasculitis, systemic lupus erythematosus or discoid lupus. Bone marrow transplantation can also result in hyposplenic function. The present inventions could therefore detect the presence of asplenia or hyposplenic function, as increased incidence of peripheral blood MN-NCE reflects absent or impaired spleen erythrophagocytosis activity.

A further aspect of the present inventions regards its potential in the field of medicine, whereby the severity of diseases associated with splenic dysfunction can be predicted based on MN-RET and/or MN-NCE measurements. The analysis of the present inventions can be performed on one or more samples from the subject, wherein the MN-NCE frequency and/or the ratio of MN-RET frequency to MN-NCE frequency is compared to either (i) a historical database that describes the typical value for subjects with the same disease or condition associated with asplenia or hyposplenic function, or (ii) based on prior measurements performed on samples obtained from the patient. Subjects that have elevated MN-NCE and/or MN-RET to MN-NCE ratios early in life, or which change substantially over a short period of time may be predicted to have a more severe form of the disease, whereby more vigorous interventions may be indicated. Conversely, subjects whose MN-NCE and/or MN-RET to MN-NCE ratios rise appreciably more slowly than usual for these diseases and conditions may be less at risk for complications and therefore less aggressive monitoring and/or intervention may be desirable.

Also contemplated is a kit to facilitate practice of the present invention. The kit can include any one or more of the above-identified reagents (present in multiple containers), materials (e.g., sample tubes), and optionally an instruction manual. A preferred kit of the present invention will contain at least one antibody that recognizes a cell surface marker for reticulocytes, at least one antibody that recognizes a surface marker for platelets, and a nucleic acid dye. More preferably, the kit can further contain a fixative agent, a buffered salt solutions, RNase, a biological standard, and suitable tubes for the collection and/or centrifugation of samples. The kit can optionally include software templates the identify parameters of operation and detection for cellular events.

EXAMPLES

The examples below are intended to exemplify the practice of the present invention but are by no means intended to limit the scope thereof.

Example 1

Rodent Blood Specimens

Sprague-Dawley rats (4-5 weeks old) were purchased from Charles River Laboratories. Animals were housed two per cage and assigned randomly to treatment groups. The animals were acclimated for approximately 2 weeks before experiments were initiated, with food and water available ad libitum throughout the acclimation and experimentation periods. Rats were treated via intraperitoneal injection with 0.9% saline for five days. Before each of the daily treatments, "low volume" blood specimens (approximately 100 μl) were collected from the tail vein of each animal into heparinized Phosphate Buffered Saline solution (i.e., blood was drawn into anticoagulant-filled 26.5 gauge needles and syringes after a brief warming period under a heat lamp). On the terminal blood harvest day, "high volume" blood samples were collected. The high volume blood collection occurred via heart puncture into anticoagulant-filled needle and syringe (approximately 1.2 blood to 5 ml anticoagulant solution). Low and high volume blood specimens were fixed for flow cytometric enumeration of MN-RET frequencies according to methods of the present invention. Fixed, coded blood specimens were stored at −80° C. until flow cytometric analysis. Heart puncture blood specimens were also added to an equal volume of heat-inactivated fetal bovine serum and smeared onto clean microscope slides, allowed to air dry, and then fixed with absolute methanol for ten minutes. Coded slides were stored in a slide box until they were processed for microscopy-based MN-RET scoring according to standard practices.

For flow cytometric analysis, rat blood samples were washed out of fixative with HBSS, and were stained according to "2-color" and "3-color" labeling methods. For the 2-color method, 20 μl of fixed, washed cells were added to flow cytometry tubes containing 80 μl of an RNase/antibody solution (contains 10 μl anti-rat CD71-FITC antibody and 10 μg RNase A per ml HBSS). Following successive 30 minute incubations at 4° C. and room temperature, cells were resuspended in 1-2 ml propidium iodide solution (1.25 μg/mlHBSS). Tubes were stored at 4° C. until analysis (same day). For 3-color analyses, the same reagents and incubation times were utilized, with the exception that anti-CD61-PE was included in the RNase/antibody solution at 5 μl per ml.

At the beginning of each day of flow cytometric analysis, instrumentation and acquisition/analysis software parameters were calibrated based on the fluorescence of a biological standard: malaria-infected rat blood (Dertinger et al., "Malaria-infected Erythrocytes Serve as Biological Standards to Ensure Reliable and Consistent Scoring of Micronucleated Erythrocytes by Flow Cytometry," *Mutat. Res.* 464: 195-200 (2000), which is hereby incorporated by reference in its entirety). This sample guided PMT voltage settings to optimally resolve parasitized (MN-like) reticulocytes, and the position of the quadrant which delineated erythrocytes with and without MN. The high prevalence of reticulocytes (i.e., FITC-positive events) and malaria-infected reticulocytes (i.e., FITC- and propidium iodide-positive events) also helped guide compensation settings. See FIG. 1.

CELLQuest software v3.3 (BD-Immunocytometry Systems, San Jose, Calif.), was utilized for data acquisition and analysis. Events were triggered on the forward scatter parameter. Data collection for each sample proceeded until the number of CD71-positive RET ($RET^{CD71+}$) equaled 20,000. The frequency of miconucleus-containing CD71-positive reticulocytes (MN-$RET^{CD71+}$) was determined for each blood sample. These data are presented herein as frequency percent.

Figure 2A:
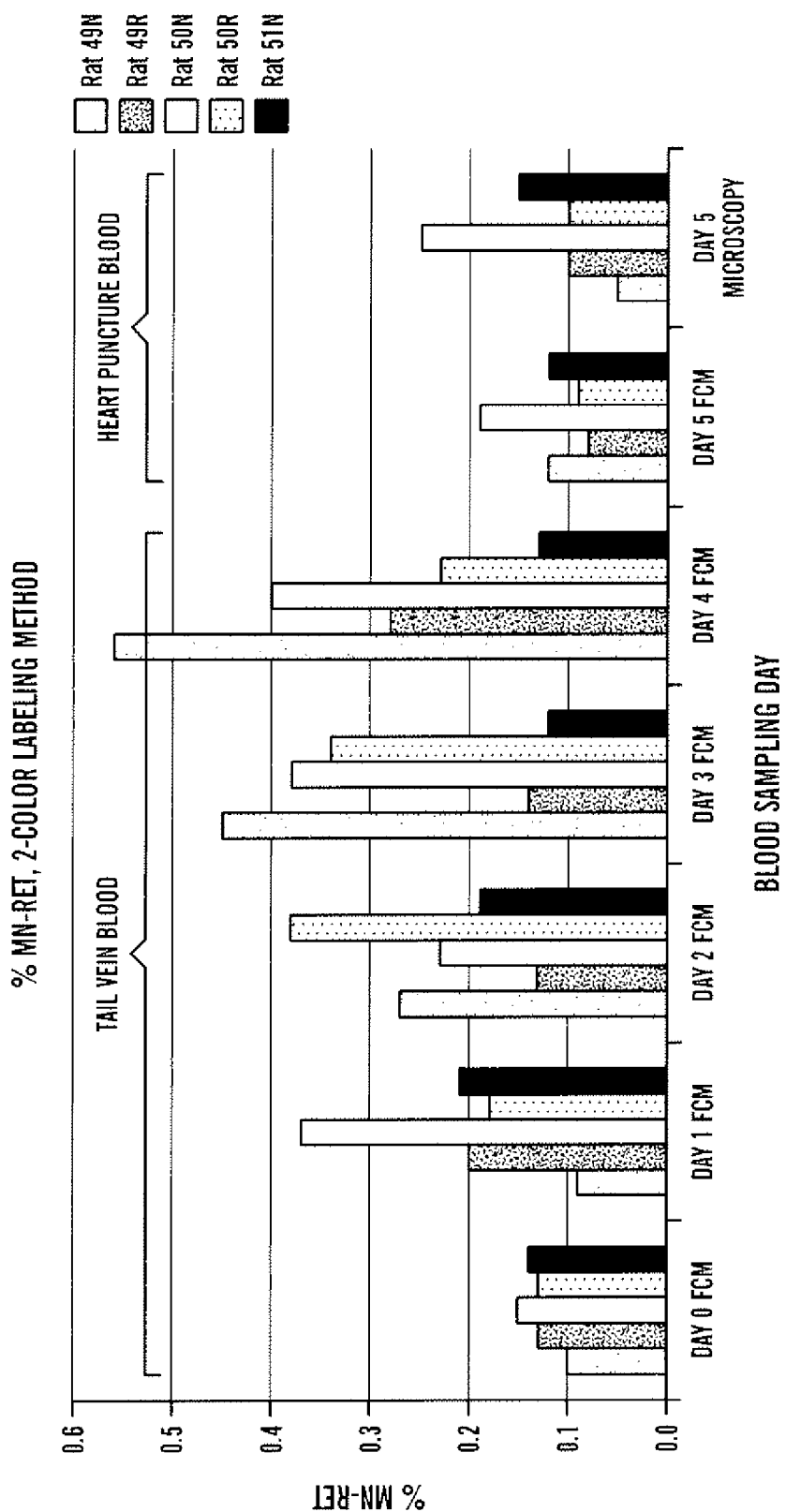
FIGS. 2A-B illustrate flow cytometry-based MN-RET frequencies graphed for blood samples obtained from five rats on six consecutive days. (Note that blood samples for Days 0-4 were collected from the tail vein, and Day 5 were collected via heart puncture). For comparison purposes, corresponding microscopy-based values for Day 5 are shown to the far right. When applied to tail vein specimens, the 2-color method (FIG. 2A) is seen to provide MN-RET values which are considerably more variable than those associated with 3-color analyses (FIG. 2B). Conversely, measurements associated with heart blood specimens were in good agreement among microscopy, and 2- and 3-color flow cytometry techniques.
Figure 2B:
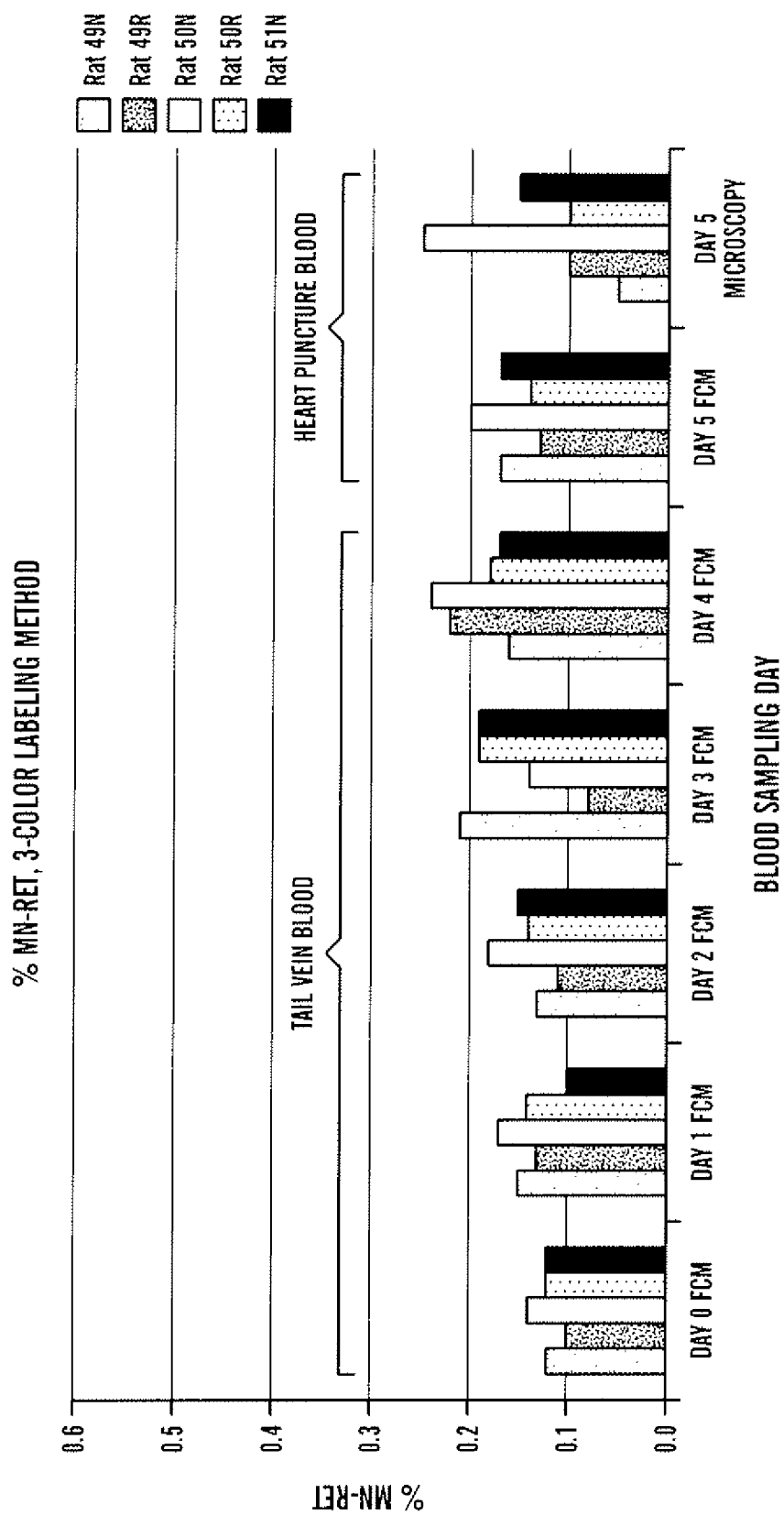

Flow cytometric MN-RET data, as well as microscopy-based data, are presented in FIG. 2. Measurements associated with the 2-color technique were found to be highly variable. Bivariate plots of anti-CD71-FITC versus propidium iodide fluorescence often showed events which fell on a 45 degree angle, starting from the major CD71-negative population, and extending into the MN-RET quadrant. The 3-color method (with the anti-platelet immunochemical reagent) demonstrated significant numbers of events that displayed similar light scatter characteristics as erythrocytes, but unlike red blood cells, exhibited anti-CD61-PE associated fluorescence. Exclusion of these events based on CD61 expression (which requires the 3-color labeling procedure) generated MN-RET data for days 0-4 which were much more reproducible than those associated with the 2-color analyses. Interestingly, little difference was observed between the 2- and 3-color methods for those samples collected via heart puncture, suggesting that activated platelets and/or platelet aggregates resulting from sub-optimal harvesting technique particularly interfere with flow cytometric rodent blood MN-RET scoring.

Example 2

Human Blood Specimens, Chemotherapy/Radiation Exposure

Absolute methanol was purchased from Fisher Scientific, Springfield, N.J. (cas no. 67-56-1). Hank's balanced salt solution (HBSS), phosphate buffered saline (PBS), and fetal bovine serum (FBS) were from MediaTech Inc., Herndon, Va. Sodium heparin (cas no. 9041-08-1), RNase A (cas no. 9001-99-4) and propidium iodide dye (cas no. 25535-16-4) were obtained from Sigma, St. Louis, Mo. Anti-human-CD71-FITC (clone M-A712), anti-CD42b-PE (clone HIP1), and anti-rat-CD71-FITC (clone OX-26) were purchased from BD-Pharmingen, San Diego, Calif. Fixed *Plasmodium berghei*-infected rat erythrocytes ("malaria-infected rat blood") were from the Rat μicroFlow® PLUS kit (Litron Laboratories, Rochester, N.Y.).

All volunteers read and signed an IRB-approved consent form. Healthy volunteers, including the splenectomized subject, were recruited at the University of Rochester Medical Center. These subjects each characterized their health status as "good", "very good" or "excellent" (as opposed to "poor" or "fair"; two current smokers were part of this group: subjects hs7 and hs9 smoke 24 or fewer cigarettes per day). See Table 1 for other characteristics. Cancer patients were recruited from the Department of Radiation Oncology, James P. Wilmot Cancer Center, University of Rochester (see Table 2 below). Each healthy subject provided one blood sample, while cancer patients provided a pre-treatment specimen and up to four additional samples drawn at approximately 24 h intervals over the course of the first week of therapy. Blood was obtained by standard venipuncture, and was added to methanol fixative according to procedures described previously (Dertinger et al., "Enumeration of Micronucleated CD71-positive Human Reticulocytes with a Single-laser Flow Cytometer," *Mutat. Res.* 515:3-14 (2002), which is hereby incorporated by reference in its entirety). These samples were stored at −80° C. for at least 16 h. On the day of FCM analysis, fixed blood samples were added to tubes containing HBSS. After centrifugation at 600×g, supernatants were decanted. Cells were resuspended by striking the tubes sharply, and cells were stored on ice until staining and analysis (same day).

TABLE 1

Reticulocyte and micronucleated cell frequencies of healthy subjects

| ID | Sex | Age | $RET^{CD71+}$ (%) | $MN\text{-}RET^{CD71+}$ (%) | MN-NCE (%) |
|---|---|---|---|---|---|
| hs1 | F | 35 | 0.08 | 0.08 | 0.001 |
| hs2 | F | 24 | 0.04 | 0.19 | 0.002 |
| hs3 | M | 47 | 0.09 | 0.14 | 0.002 |
| hs4 | M | 34 | 0.05 | 0.16 | 0.002 |
| hs5 | M | 31 | 0.14 | 0.01 | 0.001 |
| hs6 | F | 29 | 0.09 | 0.09 | 0.001 |
| hs7 | F | 48 | 0.08 | 0.07 | 0.001 |
| hs8 | M | 39 | 0.05 | 0.06 | 0.001 |
| hs9 | F | 44 | 0.51 | 0.02 | 0.001 |
| hs10 | F | 41 | 0.07 | 0.10 | 0.001 |
| hs11[a] | F | 35 | 0.14 | 0.20 | 0.142 |
| Average | | | 0.12 | 0.09 | 0.001 |
| Standard Deviation | | | 0.14 | 0.06 | 0.0005 |

Abbreviations:
RET: young (CD71-positive) reticulocytes;
MN-RET$^{CD71+}$: micronucleated reticulocytes (CD71-positive);
MN-NCE: micronucleated normochromatic erythrocytes (CD71-negative).
[a]Subject hs11 is splenectomized, and these values were not included in the average and standard deviation calculations.

which time cells were analyzed with a FACSCalibur flow cytometer (BD-Immunocytometry Systems, San Jose, Calif.).

At the beginning of each day of flow cytometric analysis, instrumentation and acquisition/analysis software parameters were calibrated based on the fluorescence of a biological standard: malaria-infected rat blood. An aliquot of this blood was treated with the same solutions used to prepare the human samples, except that anti-rat-CD71-FITC was substituted for the anti-human immunochemical reagent. After incubation and washing steps, cells were resuspended with propodium iodide solution. This sample guided PMT voltage settings to optimally resolve parasitized (MN-like) reticulocytes, and the position of the quadrant which delineated erythrocytes with and without MN. The high prevalence of reticulocytes (i.e., FITC-positive events) and malaria-infected reticulocytes (i.e., FITC- and propidium iodide-positive events) also helped guide compensation settings. See FIG. 1.

Figure 3A:
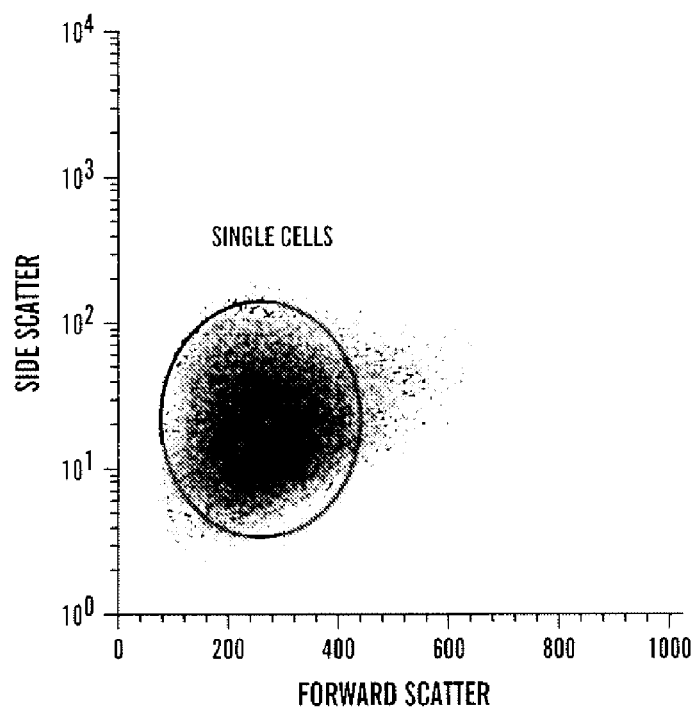
FIGS. 3A-C are bivariate graphs that illustrate the gating strategy used for mammalian blood analyses based on the 3-color labeling procedure described herein. In order to be evaluated for micronuclei, cells must fall within a light scatter region which corresponds to single unaggregated cells (FIG. 3A), exhibit a sub-2n DNA content (FIG. 3B), and lack expression of CD42b (a platelet-specific antigen) (FIG. 3C).
Figure 3B:
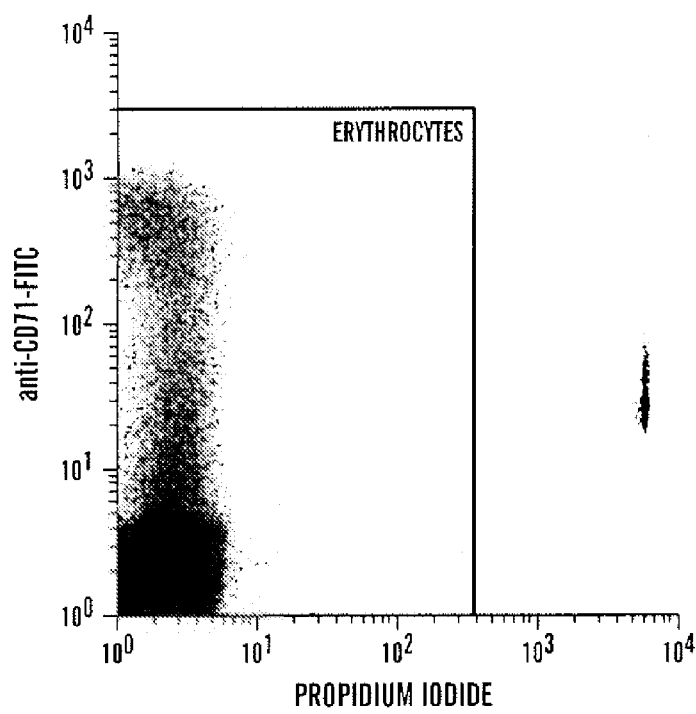
Figure 3C:
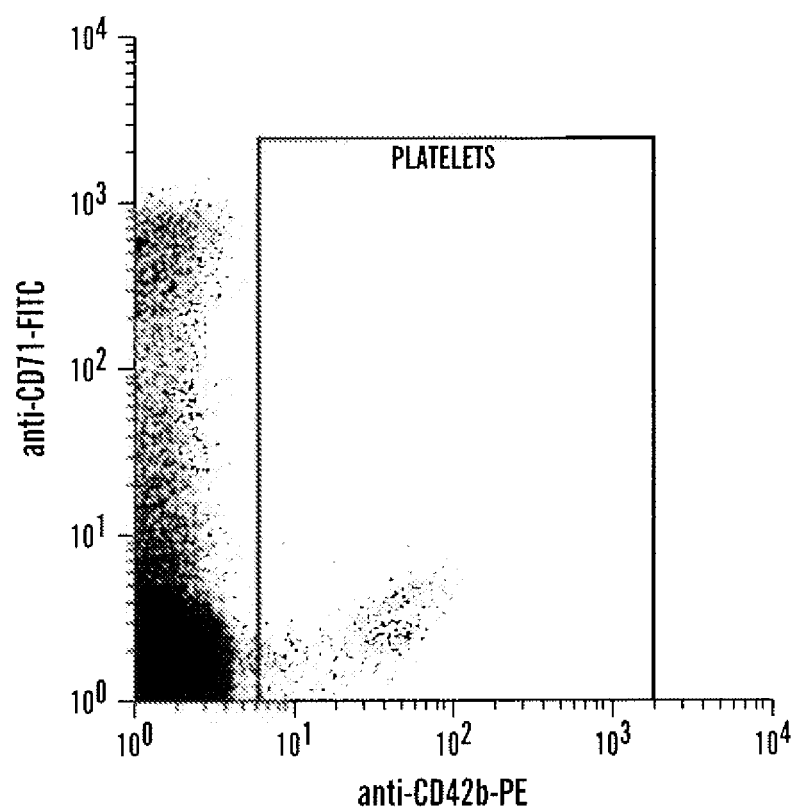

CELLQuest software v3.3 (BD-Immunocytometry Systems, San Jose, Calif.), was utilized for data acquisition and analysis. Events were triggered on the forward scatter parameter. The gating strategy for all analyses was based on three regions that were designed to exclude: (1) events smaller or larger than single cells, (2) nucleated cells based on their high (2n) DNA content, and (3) platelets based on CD42b expression. See FIG. 3. Data collection for each sample proceeded

TABLE 2

Cancer subject characteristics

| ID | Sex | Age | Diagnosis | Treatment | Field Size (cm) | Bones In Field | Total Bone Volume (cm³) | Dose (Gy per day) |
|---|---|---|---|---|---|---|---|---|
| rt1 | F | 72 | Esophoageal cancer | Radiation | 14 × 25 | Sternum, t-spine, part of upper ribs, and part of collar bone | 253 | 1.8 |
| rt2 | F | 84 | NCSL cancer IIa | Radiation | 16 × 16 | Sternum, t-spine, part of upper ribs, and part of collar bone | 215 | 2.5 |
| rt3 | M | 78 | NCSL cancer IV | Radiation | 10 × 15 | Spine | 103 | 3.0 |
| rt4 | M | 70 | NCSL cancer IIIb | Radiation | 15 × 22 | Sternum, t-spine, some ribs (especially right) | 280 | 2.5 |
| rt5 | M | 57 | Metastatic salivary gland | Radiation | 17 × 14.5 | SI joints, some pelvis | 255 | 3.5 |
| rt6 | M | 56 | Floor of mouth tumor | Radiation | 15 × 9.5 | Jaw and c-spine | 162 | 1.8 |
| ch1 | F | 56 | Small cell lung cancer | 60 mg cisplatin/m²; 100 mg etoposide/m² | | | | |
| ch2 | M | 75 | NCSL IIIb | 75 mg cisplatin/m²; 75 mg docetaxel/m² | | | | |
| ch3 | F | 44 | NCSL IIIb | 75 mg cisplatin/m²; 75 mg docetaxel/m² | | | | |

Abbreviations:
rt: radiotherapy (megavoltage external-beam photon radiation delivered with linear accelerators);
ch: chemotherapy;
NSCL: non-small cell lung;
t-spine: thoracic spine;
c-spine: cervical spine;
SI joints: sacral joints.
Note:
Total bone volumes are approximations derived from two-dimensional X-ray film.

To prepare human blood samples for flow cytometric analysis, approximately 35 µl of fixed cells were added to polypropylene tubes containing 100 µl of an RNase/antibody solution (850 µl HBSS with 1% FBS, 20 µl RNase A solution at 1 mg/ml, 100 µl anti-CD71-FITC, and 50 µl anti-CD42b-PE). Following successive 30 min incubations at 4° C. and room temperature, cells were washed with HBSS containing 1% FBS, and 1.6 ml ice-cold propidium iodide working solution was added to each tube (1.25 µg propidium iodide/ml, HBSS as diluent). Tubes were stored at 4° C. until analysis. Dye loading was conducted for at least 10 min at 4° C., after until the number of CD71-positive RET (RET$^{CD71+}$) equaled 20,000, or when the 1.6 ml sample volume was depleted, whichever came first. The number of RET$^{CD71+}$, MN-RET$^{CD71+}$, and MN-NCE was determined for each blood sample. These data are presented herein as frequency percent. Statistical analyses were performed with JMP Software (v5, SAS Institute, Cary, N.C.). For healthy volunteers, the mean and standard deviation for RET$^{CD71+}$ (%), MN-RET$^{CD71+}$ (%), and MN-NCE (%) were calculated. Note that the splenectomized subject's data were omitted from all calculations and statistical tests associated with the healthy volunteer data-set. Cancer patients' longitudinal MN-RET$^{CD71+}$ data were evaluated by least squares regression (chemotherapy patients' data were pooled and evaluated separately from radiotherapy patients' data). Based on r$^2$ values a polynomial curve of degree 3 and 2 were chosen to model the chemo- and radiotherapy MN-RET$^{CD71+}$ time-course data, respectively. ANOVA tables which accompany the JMP program's regression analyses partitioned the total variation into components, and compared the best-fit curves to a simple mean response model. A P value <0.05 was used to indicate a significant regression effect (i.e., time-dependent trend). Additionally, all cancer patients' initial (before treatment) MN-RET$^{CD71+}$ frequencies were compared to healthy volunteers'MN-RET$^{CD71+}$ values using a two-tailed Student's t-test (significance indicated by P<0.05).

Figure 4A:
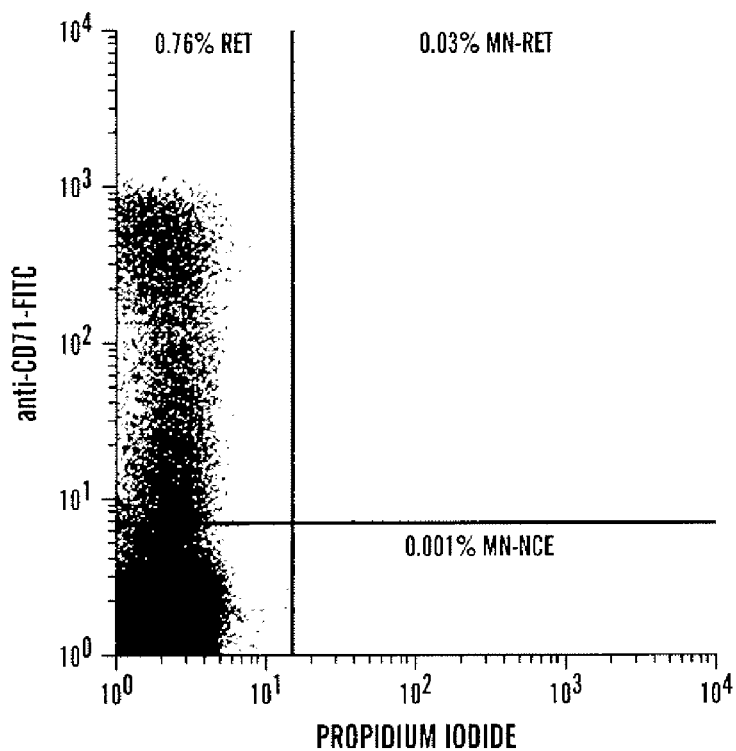
FIGS. 4A-B are bivariate graphs of blood samples from cancer patient ch1, with FIG. 4A showing a pre-treatment sample and FIG. 4B showing a sample collected 72 h after treatment with 60 mg cisplatin and 100 mg etoposide per m². CD71-associated fluorescence is graphed on the y-axis, and propidium iodide-associated with DNA content is graphed on the x-axis. Approximately 1.5 million events are shown in each bivariate plot. Comparison of FIGS. 4A-B show a reduction in reticulocytes (RET, upper left quadrant) and an increased frequency of micronucleated reticulocytes (MN-RET, upper right quadrant) in the 72 h post-treatment sample.
Figure 4B:
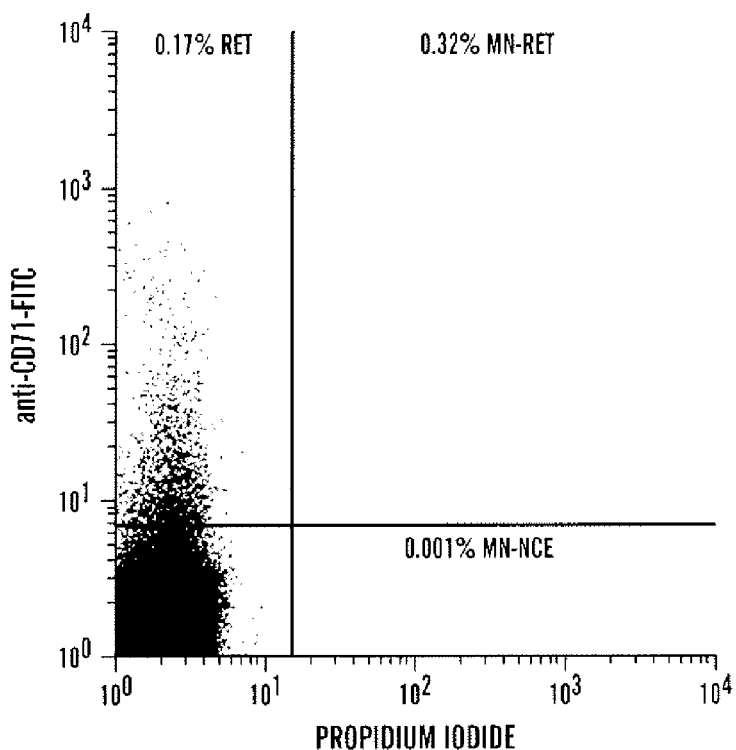

The staining procedure utilized for these studies resulted in fluorescent resolution of the target MN-RET population. Malaria-infected rat blood provided cells which mimic micronucleated erythrocytes well, and their prevalence and uniform staining characteristics were valuable for calibrating flow cytometer settings between days of analysis. These attributes also provided a means for rationally setting the position of the quadrant used to define the human erythrocyte subpopulations of interest (see FIG. 4A-B).

Figure 5:
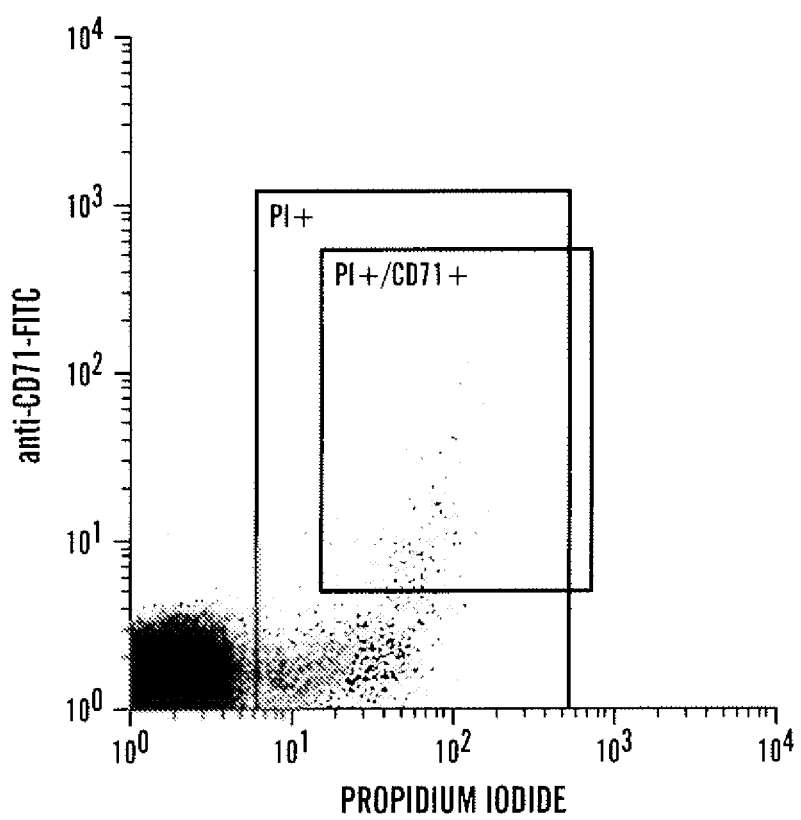
FIG. 5 is a bivariate graph illustrating the resolution of propidium iodide-positive erythrocytes (i.e., RNA positive RET) and anti-CD71-FITC-positive erythrocytes (i.e., very immature RET) from normochromatic erythrocytes. For this analysis, fixed samples were treated with the standard reagents as described; however, RNase was omitted. These analyses suggest that it is approximately the youngest 10% of RNA-positive human RET in peripheral blood circulation which are labeled with the anti-CD71 reagent.

The results from healthy volunteers are presented in Table 1 above. Based on the average RET$^{CD71+}$ (%) value for these subjects, and also on analyses whereby reticulocyte frequencies were measured based on RNA-associated fluorescence, we estimate that the anti-CD71-FITC reagent labeled approximately the youngest 10% of RNA-positive RET (see FIG. 5). For eusplenic subjects, this young cohort of erythrocytes exhibited an average value of 0.09% MN-RET$^{CD71+}$. The efficiency by which the human spleen removes MN from circulation was demonstrated by the extremely low values observed for these healthy subjects' mature erythrocytes (0.001-0.002% MN-NCE). In addition to these samples, blood from a splenectomized but otherwise healthy individual was analyzed (subject hs11; MN-RET$^{CD71+}$=0.20%).

Figure 6:
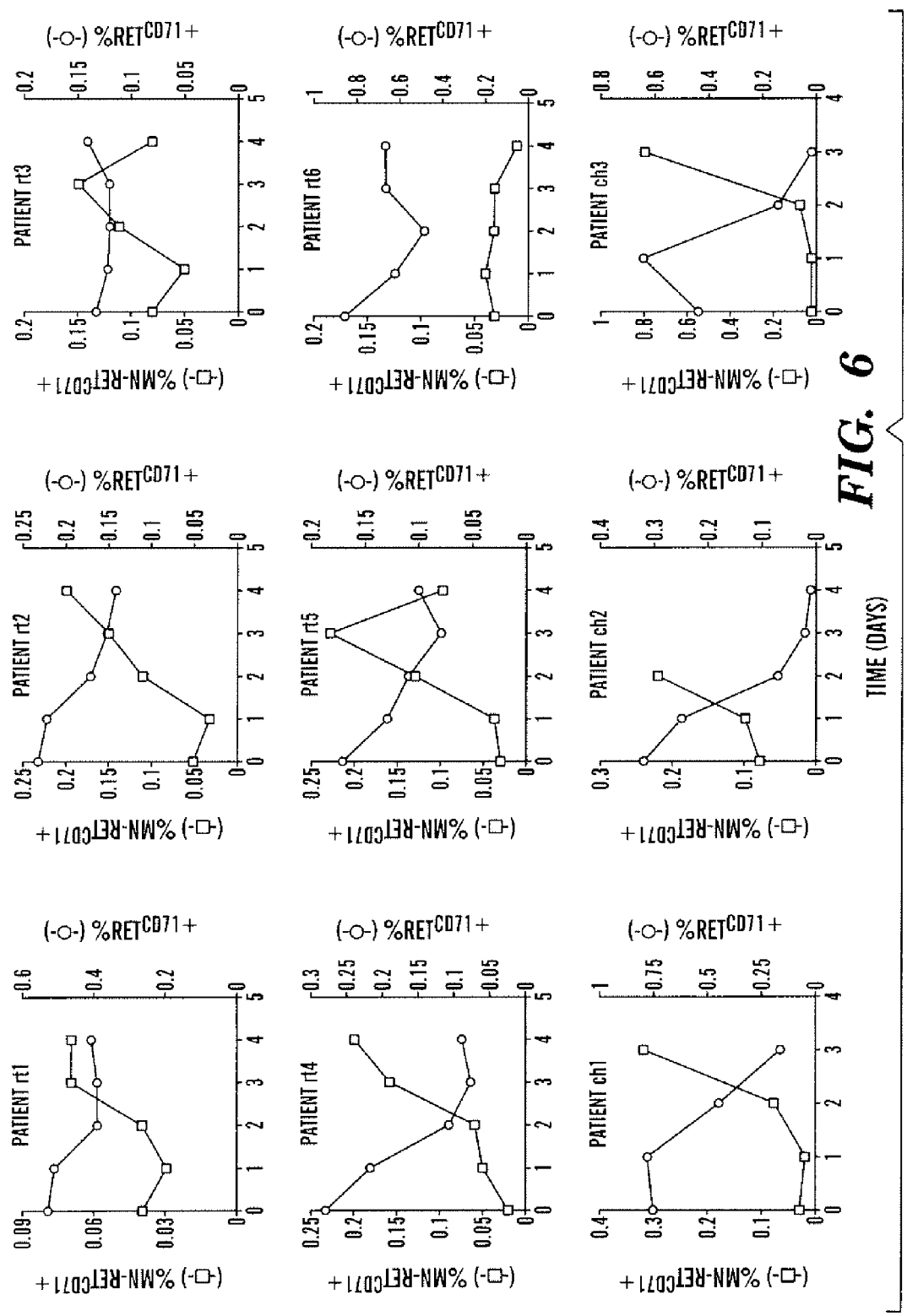
FIG. 6 illustrates CD71-positive micronucleated reticulocytes (MN-RET$^{CD+}$ (%)) and CD71-positive reticulocytes (RET$^{CD71+}$ (%)) which are graphed for nine cancer therapy patient (rt: radiotherapy; ch: chemotherapy). While the frequency of RET$^{CD71+}$ was generally found to decline over the first week of treatment, higher incidences of MN-RET$^{CD71+}$ were observed. The time-dependent increase in MN-RET$^{CD71+}$ (%) for chemo- and radiotherapy cancer patients are statistically significant (P=0.0166 and 0.0081, respectively).

As expected, chemo- and radiotherapy reduced the frequency of RET$^{CD71+}$ over the course of cancer treatment (see FIG. 6). The proportion of red marrow space that was subjected to treatment was likely an important determinant for the range of responses observed. For instance, chemotherapy subjects, who presumably received systemic exposure, showed the greatest reduction to RET$^{CD71+}$ (%). In fact, in the case of subject ch2, treatment-related reduction to peripheral blood RET$^{CD71+}$ was so severe as to preclude an accurate determination of MN-RET$^{CD71+}$ frequency three and four days post-treatment (RET$^{CD71+}$ (%)=0.01).

Regarding cancer patients' MN-RET$^{CD71+}$ frequencies, no significant difference was observed between pre-treatment values and those of the healthy volunteers. However, as illustrated by FIG. 6, the majority of cancer patients demonstrated elevated MN-RET$^{CD71+}$ frequencies over the course of therapy. Regression analyses indicate that these time-dependent increases in MN-RET$^{CD71+}$ are statistically significant (P=0.0166 and 0.0081 for pooled chemo- and radiotherapy patients, respectively).

Figure 7:
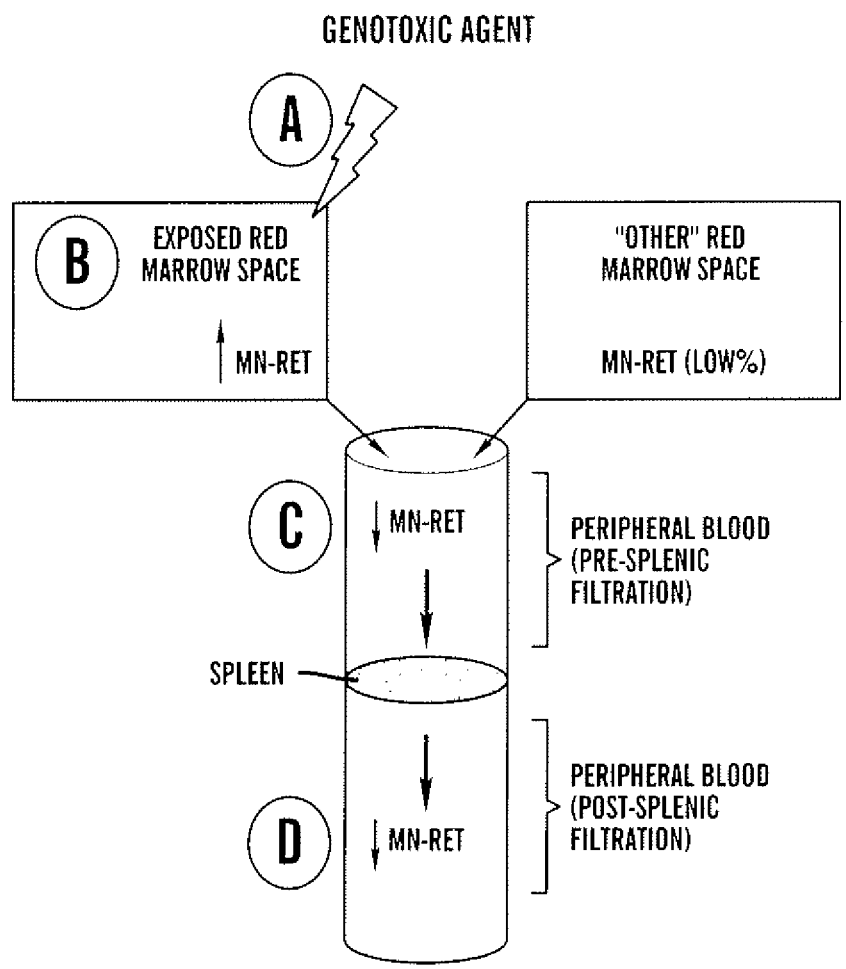
FIG. 7 illustrates a model describing the major factors that affect micronucleated reticulocyte (MN-RET) frequency in human peripheral blood. (A) Radiation intensity or chemical dose; (B) host-specific factors which dictate intrinsic chemo- or radiosensitivity; (C) dilution effect as induced MN-RET enter peripheral blood circulation with reticulocytes derived from unexposed red marrow site(s); (D) erythrophagocytosis activity (especially the spleen) removes MN-containing red blood cells from circulation.

As with the RET$^{CD71+}$ population, MN-RET$^{CD71+}$ frequencies were likely influenced by the proportion of red marrow space exposed. Thus, in the case of radiotherapy, MN-induction was muted to the extent that other (non-exposed) sites of erythropoiesis supplied the peripheral blood compartment with MN-RET$^{CD71+}$ at a baseline frequency. For instance, the little or no change in MN-RET$^{CD71+}$ (%) for subjects rt3 (spine irradiation) and rt6 (jaw/spine irradiation) is likely related to the low proportion of active hematopoietic red marrow which was exposed (as reflected by a lack of change in RET$^{CD71+}$ (%)). Conversely, the higher MN responses observed for patients undergoing chemotherapy or large field chest irradiation was likely due to the large amounts of red marrow exposure that was achieved. In addition to exposure field location/size, another factor which may help explain modest or no observed effects for subjects rt1 and rt6 is a relatively lower radiation intensity (1.8 Gy per day). A simple model which describes the major variables which appear to affect peripheral blood MN-RET$^{CD71+}$ frequency is illustrated by FIG. 7.

Data presented herein support the concept that the incidence of MN-RET in human peripheral blood circulation can be used to index recent cytogenetic damage. Increased MN-RET$^{CD71+}$ values were evident 2-4 days after initiation of treatment, and this is in agreement with the kinetics of erythroblast differentiation and the entry of newly formed erythrocytes into the peripheral blood compartment (Hillman and Finch, "Erythropoiesis: Normal and Abnormal," *Semin. Hematol.* 4:327-336 (1967), which is hereby incorporated by reference in its entirety). This is made possible by an analytical system which is capable of restricting analyses to the most immature fraction of RET. The rarity of RET$^{CD71+}$, coupled with the low frequency of MN events, makes the high-throughput nature of the scoring system an essential characteristic. For instance, the time required to collect data on the flow cytometer was approximately 25 min per sample. Even with these relatively lengthy data acquisition times, the number of RET$^{CD71+}$ interrogated for MN per sample was typically about 10,000. Methods for enriching blood for newly formed erythrocytes have been described in the literature (Abramsson-Zetterberg et al., "Human Cytogenetic Biomonitoring Using Flow-Cytometric Analysis of Micronuclei in Transferrin-Positive Immature Peripheral Blood Reticulocytes," *Environ. Mol. Mutagen.* 36:22-31 (2000); Choy and MacGregor, "Density-gradient Enrichment of Newly-Formed Mouse Erythrocytes: Application to the Micronucleus Test," *Mutat. Res.* 130:159-164 (1984), which is hereby incorporated by reference in its entirety), and these could potentially lower flow cytometer data acquisition time, and also increase the numbers of RET interrogated. However, an objective of the present invention has been to establish a method that requires as few manipulations with whole, unfixed human blood as possible. That is, a priority was placed on keeping the procedure simple and reproducible for the medical technologist in the clinical environment.

The simplicity of the processing steps may be of practical importance for using the technique in any clinical and/or biomonitoring applications. The invention described herein addresses the relatively lengthy flow cytometry data acquisition times associated flow cytometric analyses that do not include a physical RET enrichment scheme. Instead, a technique for improving sample throughput capabilities is demonstrated in Example 3 below.

The blood samples from 10 healthy volunteers were important for estimating baseline RET$^{CD71+}$, MN-RET$^{CD71+}$, and MN-NCE values. The average frequency of MN-RET$^{CD71+}$ was similar, although somewhat lower, than values observed in the bone marrow or in the peripheral blood circulation of splenectomized human subjects (0.09% compared to approximately 0.2-0.3%; see (Goetz et al., "Relationship Between Experimental Results in Mammals and Man: Cytogenetic Analysis of Bone Marrow Injury Induced by a Single Dose of Cyclophosphamide," *Mutat. Res.* 31:247-254 (1975); Krogh Jensen and Nyfors, "Cytogenetic Effect of Methotrexate on Human Cells In Vivo," *Mutat. Res.* 64:339-343 (1979); Abe et al., "Micronuclei in Human Bone Marrow Cells: Evaluation of the Micronucleus Test Using Human Leukemia Patients Treated with Antileukemic Agents," *Mutat. Res.* 130:113-120 (1984); Schlegel et al., "Assessment of Cytogenetic Damage by Quantitation of Micronuclei in Human Peripheral Blood Erythrocytes," Cancer Res. 46:3717-3721 (1986); Smith et al. ("Micronucleated Erythrocytes as an Index of Cytogenetic Damage in Humans: Demographic and Dietary Factors Associated with Micronucleated Erythrocytes in Splenectomized Subjects," Cancer Res. 50:5049-5054 (1990); and MacGregor et al., "Spontaneous Genetic Damage in Man: Evaluation of Interindividual Variability, Relationship Among Markers of Damage, and Influence of Nutritional Status," *Mutat. Res.* 377:125-135 (1997), each of which is hereby incorporated by reference in its entirety). This is likely related to erythrophagocytosis activity, which may not be fully negated by restricting analyses to $RET^{CD71+}$. Even so, when compared to MN-NCE values (<0.002%), the average MN-$RET^{CD71+}$ frequency of 0.09% provides evidence that the analytical system described herein does effectively minimize the impact that spleen function has on peripheral blood MN frequency.

Similar to Smith et al. ("Micronucleated Erythrocytes as an Index of Cytogenetic Damage in Humans: Demographic and Dietary Factors Associated with Micronucleated Erythrocytes in Splenectomized Subjects," Cancer Res. 50:5049-5054 (1990), which is hereby incorporated by reference in its entirety), a greater than 10-fold range of MN-$RET^{CD71+}$ frequencies in presumably healthy volunteers was observed. Knowledge of this extent of variation in spontaneous MN-$RET^{CD71+}$ frequency was valuable information for designing experiments to evaluate genotoxicant-induced MN. That is, these data clearly indicated the desirability of obtaining pre-treatment blood samples when studying oncology patients. As with the healthy subjects, pre-treatment MN-$RET^{CD71+}$ frequencies of cancer patients were indeed variable (range=0.02-0.17%). Even so, pre-treatment samples served as patient-specific controls, and were helpful for assessing treatment-related changes to MN frequency in the relatively small number of subjects studied.

For the present study, cancer patients' blood samples were used for the express purpose of evaluating the FCM-based scoring systems' ability to detect MN induced by known physical and chemical genotoxic agents. Many other reports exist in which the micronucleus endpoint has been measured in cancer patients. Since the clinical efficacy of ionizing radiation and the majority of antineoplastic drugs has most often been attributed to their ability to cause irreparable DNA damage, MN formation has been evaluated as a nonclonogenic endpoint that might provide valuable patient-specific information regarding sensitivity to treatment (Bhattathiri et al., "Serial Cytological Assay of Micronucleus Induction: A New Tool to Predict Human Cancer Radiosensitivity," *Radiother. Oncol.* 41:139-142 (1996); and Guo et al., "A Significant Correlation Between Clonogenic Radiosensitivity and the Simultaneous Assessment of Micronucleus and Apoptotic Cell Frequencies," *Int. J. Radiation Biol.* 75:857-864 (1999), each of which is hereby incorporated by reference in its entirety). Other reports have suggested that the endpoint may have prognostic value (Zolzer et al., "Changes in S-phase Fraction and Micronucleus Frequency as Prognostic Factors in Radiotherapy of Cervical Carcinoma," Radiother. Oncol. 36:128-132 (1995); Widel et al., "The Increment of Micronucleus Frequency in Cervical Carcinoma During Irradiation In Vivo and Its Prognostic Value for Tumor Radiocurability," Br. J. Cancer 80:1599-1607 (1999); Widel et al., "Micronucleus Assay In Vivo Provides Significant Prognostic Information in Human Cervical Carcinoma: The Updated Analysis," *Int. J. Radiat. Biol.* 77:631-636 (2001), each of which is hereby incorporated by reference in its entirety), or that it may be valuable for detecting predisposition to certain cancers (Doneda et al., "High Spontaneous Chromosome Damage in Lymphocytes From Patients With Hereditary Megaduodenum," *Mutat. Res.* 348:33-36 (1995); Berg-Drewniok et al., "Increased Spontaneous Formation of Micronuclei in Cultured Fibroblasts of First-degree Relatives of Familial Melanoma Patients," *Cancer Genet. Cytogenet.* 97:106-110 (1997); Scott et al., "Radiation-induced Micronucleus Induction in Lymphocytes Identifies a High Frequency of Radiosensitive Cases Among Breast Cancer Patients: A Test for Predisposition?" *Br. J. Cancer* 77:614-620 (1998); Burrill et al., "Heritability of Chromosome Radiosensitivity in Breast Cancer Patients: A Pilot Study with the Lymphocyte Micronucleus Assay," *Int. J. Radiat. Biol.* 76:1617-1619 (2000), each of which is hereby incorporated by reference in its entirety). For these various studies, MN have been studied in tumor biopsy material, as well as in blood lymphocytes which have been stimulated to divide in culture (Fenech, "The Cytokinesis-block Micronucleus Technique: A Detailed Description of the Method and its Application to Genotoxicity Studies in Human Populations," *Mutat. Res.* 285:35-44 (1993), each of which is hereby incorporated by reference in its entirety).

Based on data reported herein, CD71-positive RET in peripheral blood circulation represent an alternate target cell population which can be used to assess DNA damaging activity. Analyses based on these cells offer several advantages, including: minimally invasive cell harvest; low blood volume requirement; simple fixation/staining procedures; and unbiased, automated scoring. MN-$RET^{CD71+}$ measurements may prove useful to researchers and clinicians who are involved in cancer susceptibility testing, prognosis, or treatment optimization. Additionally, these measurements may represent a minimally invasive biomonitoring tool for assessing occupational, environmental, or nutritional factors that might be expected to have genotoxic consequences (MacGregor et al., "Spontaneous Genetic Damage in Man: Evaluation of Interindividual Variability, Relationship Among Markers of Damage, and Influence of Nutritional Status," *Mutat. Res.* 377:125-135 (1997); Anwar et al., "Chromosomal Aberrations and Micronucleus Frequency in Nurses Occupationally Exposed to Cytotoxic Drugs," *Mutagenesis* 9:315-317 (1994); Ilyinskikh et al., "Micronucleus Test of Erythrocytes and Lymphocytes in the Blood of the People Living in the Radiation Pollution Zone as a Result of the Accident at the Siberian Chemical Plant on Apr. 6, 1993," *Mutat. Res.* 36:173-178 (1996); Maffei et al., "Micronuclei Frequencies in Hospital Workers Occupationally Exposed to Low Levels of Ionizing Radiation: Influence of Smoking Status and Other Factors," *Mutagenesis* 17:405-409 (2002); Fenech, "Biomarkers of Genetic Damage for Cancer Epidemiology," *Toxicology* 181-182:411-416 (2002), each of which is hereby incorporated by reference in its entirety).

Example 3

High Speed MN-RET Data Acquisition

The Informed consent was obtained from a small cell lung cancer patient who was recruited from the James P. Wilmot Cancer Center, University of Rochester. The cancer patient provided a blood sample just prior to, and again three days after treatment with 60 mg cisplatin/$m^2$ and 100 mg etoposide/$m^2$. Blood was obtained by standard venipuncture, and was added to methanol fixative according to the present invention. Fixed samples were stored at −80° C. for at least one day before flow cytometric analysis.

Fixed human blood specimens (1-2 ml) were added to tubes containing 12 ml ice-cold HBSS and cells were collected by centrifugation. Supernatants were decanted and pellets were tapped loose. For 2-color labeling, 35 µl cells were added to polypropylene tubes containing 100 µl of an RNase/antibody solution (900 µl HBSS with 1% FBS, 100 µl anti-CD71-FITC, and RNase A at 20 µg/ml). Following successive 30 minute incubations at 4° C. and room temperature, cells were washed with 5 ml HBSS containing 1% FBS, and finally resuspended in 1.5 ml propidium iodide solution. Stained samples were stored at 4° C. until analysis (same day). For 3-color analyses, similar procedures were used, except that 50 µl anti-CD42b-PE replaced 50 µl of HBSS with 1% FBS in the RNase/antibody solution. Also, for the alternative "high density/FL1-thresholding technique", washed cells were concentrated with vigorous decanting after the initial centrifugation step, and entire cell pellets were added to polypropylene tubes containing RNase/antibodies. By high density, it is believed that the resulting cell concentration achieved is about 80 million cells/ml. This is roughly 15 times greater than the cell density utilized in the preceding examples.

At the beginning of each day of flow cytometric analysis, instrumentation and acquisition/analysis software parameters were calibrated based on the fluorescence of a biological standard: malaria-infected mouse or rat blood. An aliquot of this blood was incubated with the same RNase, anti-CD71-FITC, and propidium iodide solutions used for test samples (except that anti-rat-CD71-FITC was substituted for the anti-human immunochemical reagent). As described previously, these samples guided PMT voltage and electronic compensation settings to optimally resolve parasitized (MN-like) reticulocytes, and also guided the position of the quadrant which delineated erythrocytes with and without MN.

Data acquisition and analyses were performed using a FACSCalibur flow cytometer providing 488 nm excitation, running CellQuest software (v3.3). Anti-CD71-FITC, anti-platelet-PE, and propidium iodide fluorescence signals were detected in the FL1, FL2, and FL3 channels, respectively. Unless otherwise stated, events were triggered with a FSC threshold so that all cell-sized events were collected. For human blood samples analyzed according to the high density/FL1-thresholding technique, events were triggered using an FL1 threshold which eliminated CD71-negative erythrocytes (NCE) from consideration. The stop mode was set so that 20,000 CD71-positive reticulocytes were analyzed for MN per sample.

Figure 8:
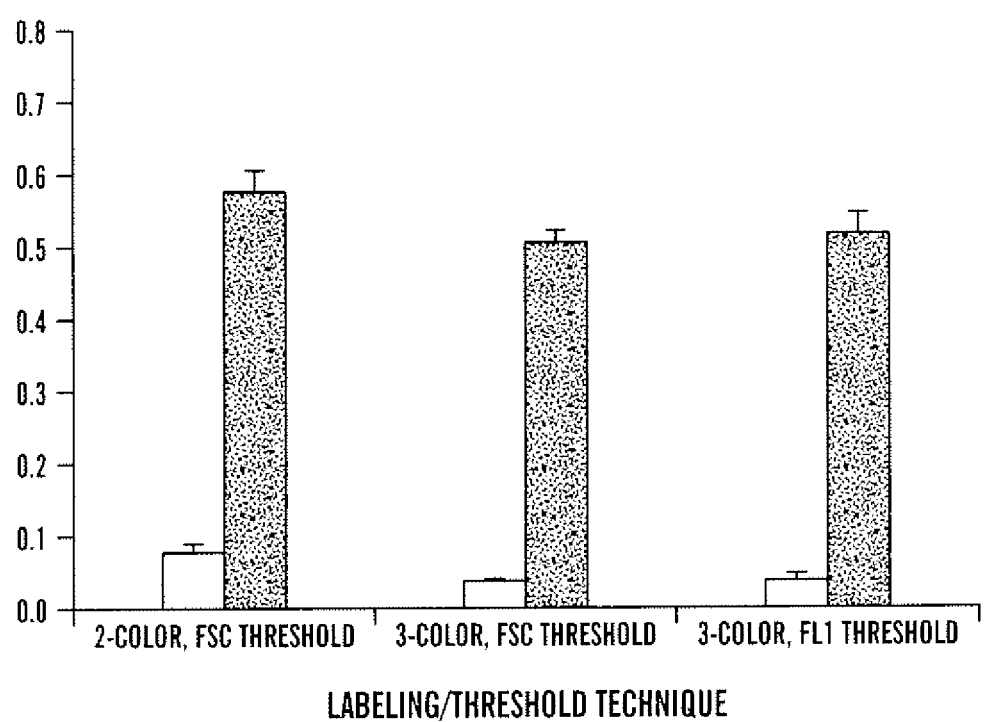
FIG. 8 is a graph illustrating average flow cytometry-based micronucleated reticulocyte frequencies (with S.E.M. bars) for human blood samples obtained from a chemotherapy patient before and after treatment. These specimens were analyzed in triplicate using the 2-color and 3-color labeling procedures (left and center bars). Additionally, triplicate samples were analyzed at very high density using the 3-color procedure in conjunction with FL1 thresholding (right bars). The 2-color specimens exhibited spurious events in the MN-RET quadrant, and consequently these values tended to be higher than their 3-color counterparts. The high density/FL1 thresholding technique was observed to reduce data acquisition time and the size of FCM files significantly.

Triplicate blood specimens were analyzed according to 2- and 3-color labeling procedures as described above. MN-RET values for the 3-color method were consistently lower than those for corresponding 2-color analyses (FIG. 8). These quantitative differences suggested that although these specimens were collected via arm venipuncture, and hence would not be expected to have large numbers of activated platelets, platelets none-the-less interfered with MN-RET measurements. Aside from the difference observed between 2- and 3-color MN-RET values, fluorescence microscopy confirmed the identity of CD42b-positive events as platelets and platelet aggregates.

The specimens from this chemotherapy patient were further analyzed according to the 3-color labeling scheme, but at very high cell densities. These extreme cell densities would ordinarily be above the FACSCalibur's 7,000 events per second maximum rate. This was addressed by changing from a FSC to an FL1 trigger, and by adjusting the threshold so that only CD71-positive erythrocytes were evaluated. This modification generated MN-RET values that were in good agreement with those produced with the FSC threshold/lower density analyses (3-color). The main benefit of the high density technique was that the average time to interrogate 20,000 RET per sample was reduced from approximately 24 minutes on average to less than 4 minutes. Furthermore, the size of the data files was reduced from ≥105 Mb to less than 1 Mb. FIG. 8.

Example 4

Assessment of Splenic Filtration Function

Discarded EDTA-blood specimens from unselected children with documented HbSS or HbSC disease were fixed according to methods of the present invention. Codes specimens were shipped to Litron Laboratories on dry ice for flow cyometric analysis.

Fixed blood specimens (2 ml) were combined with 12 ml ice-cold HBSS and cells were collected by centrifugation. Supernatants were decanted and pellets were tapped loose. The 3-color labeling procedure was utilized whereby approximately 35 µl of washed cells were added to polypropylene tubes containing 100 µl of an RNase/antibody solution (850 µl HBSS with 1% FBS, 100 µl anti-CD71-FITC, 50 µl anti-CD42b-PE, and RNase A at 20 µg/ml). Following successive 30 minute incubations at 4° C. and room temperature, cells were washed with 5 ml HBSS containing 1% FBS, and finally resuspended in 1.5 ml propidium iodide solution. Stained samples were stored at 4° C. until analysis (same day).

At the beginning of each day of flow cytometric analysis, instrumentation and acquisition/analysis software parameters were calibrated based on the fluorescence of a biological standard: malaria-infected mouse or rat blood. An aliquot of this blood was incubated with the same RNase, anti-CD71-FITC, and propidium iodide solutions used for test samples (except that anti-rat-CD71-FITC was substituted for the anti-human immunochemical reagent). As described previously, these samples guided PMT voltage and electronic compensation settings to optimally resolve parasitized (MN-like) reticulocytes, and also guided the position of the quadrant which delineated erythrocytes with and without MN.

Data acquisition and analyses were performed using a FACSCalibur flow cytometer providing 488 nm excitation, running CellQuest software (v3.3). Anti-CD71-FITC, anti-platelet-PE, and propidium iodide fluorescence signals were detected in the FL1, FL2, and FL3 channels, respectively. Events were triggered with a FSC threshold so that all cell-sized events were collected. The stop mode was set so that 1,000,000 erythrocytes were analyzed for MN per sample.

Figure 9A:
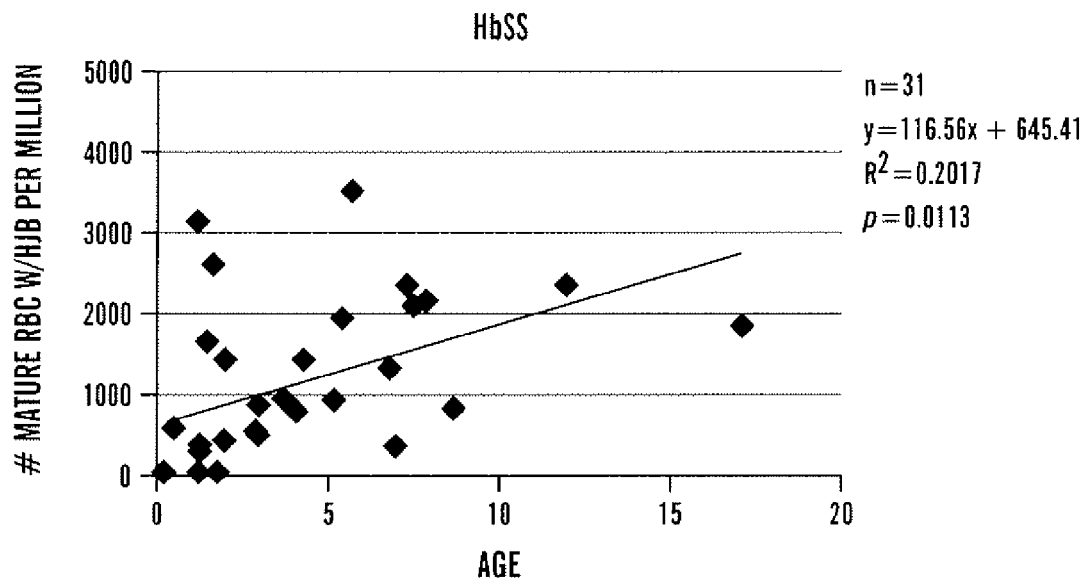
FIGS. 9A-B illustrate the frequency of MN-NCE versus patient age. (MN-NCE are labeled as the number of mature red blood cells with Howell-Jolly bodies per million cells.) FIG. 9A corresponds to sickle cell anemia patients with the most severe form of the disease, HbSS.
Figure 9B:
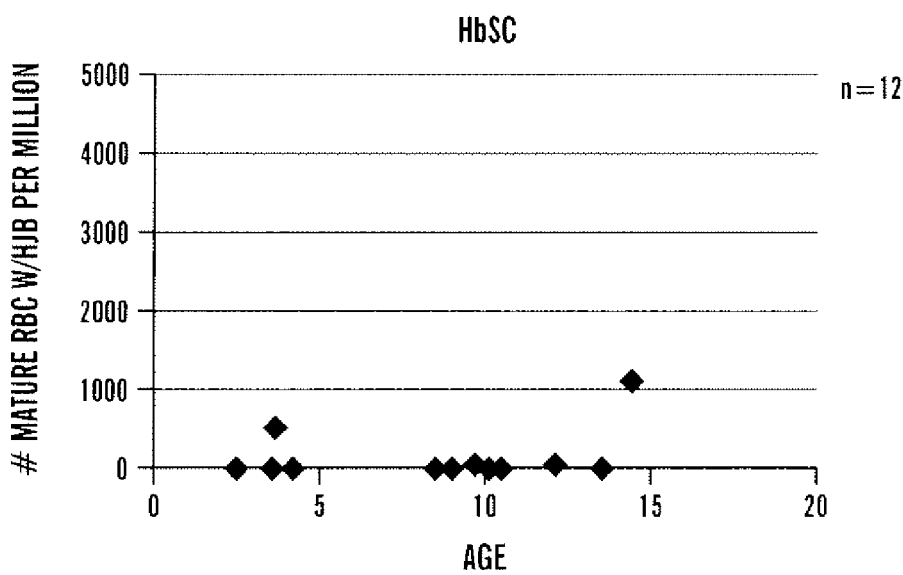

The frequency of MN-NCE for pediatric patients with documented HbSS and HbSC disease are presented in FIGS. 9A-B, respectively. HbSS patients ranged in age from 0.2 to 17.1 years, and would be expected to provide varying degrees of accumulated vaso-occlusive damage to the spleen. As expected, an age-dependent increase in HJB values for HbSS patients is statistically significant (p=0.0113, linear regression analysis, JMP software v5). On the other hand, specimens from 12 HbSC patients did not exhibit a significant age-dependent effect on MN-NCE values. In fact, for ten of twelve HbSC patients, MN-NCE values are in the same range as those observed in healthy volunteers (less than $100 \times 10^{-6}$). Taken together, these 43 specimens lend support the premise that MN-NCE measurements provided by the present invention are indicative of splenic erythrophagocytosis function, and that there may be prognostic value to these measurements, as the HbSS genotype is known to have a more severe clinical course relative to HbSC disease. Thus, it is likely that multivariate models designed to predict sickle cell disease severity would benefit from these spleen function data.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for the enumeration of micronucleated erythrocyte populations, the method comprising:
    providing a blood or bone marrow sample that is enriched for erythrocyte populations comprising one or more of mature normochromatic erythrocytes, reticulocytes, micronucleated normochromatic erythrocytes, and micronucleated reticulocytes, wherein the erythrocyte populations in the enriched sample are rendered permeable;
    contacting the sample with (i) RNase to degrade RNA in the permeable erythrocyte populations, (ii) a first reagent comprising a fluorescent label and having binding specificity for a surface marker for reticulocytes, (iii) a second reagent comprising a fluorescent label and having binding specificity for a surface marker for platelets, and (iv) a nucleic acid staining dye, wherein said contacting with RNase is carried out prior to said contacting with the nucleic acid staining dye, and wherein the fluorescent emission spectra of the fluorescent labels of the first and second reagents and the nucleic acid staining dye are distinguishable from one another;
    exciting the nucleic acid staining dye, the fluorescent label associated with the reticulocytes, and the fluorescent label associated with platelets using light of appropriate excitation wavelength for both the nucleic acid staining dye and the fluorescent labels to produce fluorescent emission; and
    detecting the fluorescent emission and light scatter produced by the erythrocyte populations and platelets, and counting the number of cells from one or more erythrocyte populations in said sample while excluding scoring events caused by platelets and platelet-associated aggregates from scoring events for micronucleated normochromatic erythrocytes and/or micronucleated reticulocytes.

2. The method according to claim 1 wherein the erythrocyte populations are collectively present at a concentration of greater than about 30 million cells/ml.

3. The method according to claim 1 wherein the erythrocyte populations are collectively present at a concentration of greater than about 50 million cells/ml.

4. The method according to claim 1, wherein said contacting with RNase, the first reagent, the second reagent, and the nucleic acid staining dye are carried out sequentially in the recited order.

5. The method according to claim 4 further comprising:
    removing first and second reagents not bound to cells in the contacted sample prior to said contacting with the nucleic acid staining dye.

6. The method according to claim 1, wherein said contacting with the RNase and the first and second reagents is carried out simultaneously.

7. The method according to claim 6 further comprising:
    removing first and second reagents not bound to cells in the contacted sample prior to said contacting with the nucleic acid staining dye.

8. The method according to claim 1 wherein said counting is carried out for reticulocytes and micronucleated reticulocytes.

9. The method according to claim 1 wherein said providing comprises:
    obtaining a peripheral blood or bone marrow sample from a mammal;
    passing the sample through an enrichment medium and recovering the enriched erythrocyte populations; and
    treating the erythrocyte populations with a reagent that renders the erythrocyte populations permeable.

10. The method according to claim 9 further comprising:
    administering a DNA-damaging agent to the mammal prior to said obtaining.

11. The method according to claim 9, wherein the reagent that renders the erythrocyte populations permeable is an alcohol at a temperature of from about −40° C. to about −90° C.

12. The method according to claim 1 wherein the surface marker for reticulocytes is CD71.

13. The method according to claim 1 wherein the surface marker for platelets is CD9, CDw17, CD29, CD31, CD32, CD41, CD42a, CD42b, CD42c, CD42d, CD43, CD46, CD49f, CD51, CD60a, CD61, CD62P, CD63, CD69, CD82, CD98, CD102, CD110, CD112, CDw119, CD120a, CD128a, CD128b, CD130, CD132, CD140a, CD141, CD148, CD151, CD165, CD184, CD226, or CD245.

14. The method according to claim 1 wherein said exciting and detecting are carried out using a flow cytometer comprising either a single laser or two or more lasers.

15. The method according to claim 14 further comprising:
    calibrating the flow cytometer using a biological standard which has been treated in parallel with the sample.

16. The method according to claim 15 wherein said calibrating comprises setting photomultiplier tube voltage, setting electronic compensation parameters, defining the position of regions that distinguish a micronucleus-containing erythrocyte from a mature normochromatic erythrocyte or a reticulocyte, and combinations thereof.

17. The method according to claim 15 wherein the biological standard is an erythrocyte sample obtained from a malaria-infected mammal.

18. The method according to claim 1 wherein said counting is carried out for reticulocytes, micronucleated reticulocytes, normochromatic erythrocytes, and micronucleated normochromatic erythrocytes.

* * * * *